United States Patent [19]

Cundall et al.

[11] 4,322,347
[45] Mar. 30, 1982

[54] 2-CARBAMOYLOXYMETHYL-PENICILLIN DERIVATIVES

[75] Inventors: Robert L. Cundall, Liverpool; Derek Walker, Jamesville, both of N.Y.

[73] Assignee: Bristol-Myers Company, New York, N.Y.

[21] Appl. No.: 893,092

[22] Filed: Apr. 3, 1978

[51] Int. Cl.$^3$ .................. C07D 499/32; A61K 31/38; C07D 501/14

[52] U.S. Cl. ................. 260/239.1; 424/246; 424/271; 544/16; 544/18; 544/21; 544/22; 544/23; 544/24; 544/25; 544/30; 548/178

[58] Field of Search ...................... 548/178; 260/239.1

[56] References Cited

U.S. PATENT DOCUMENTS

| | | | |
|---|---|---|---|
| 3,275,626 | 9/1966 | Morin et al. | 260/239.1 |
| 3,714,156 | 1/1973 | Rapoport | 548/178 |
| 3,997,533 | 12/1976 | Kabbe et al. | 260/239.1 |
| 4,010,156 | 3/1977 | Nudelman et al. | 260/239.1 |
| 4,182,711 | 1/1980 | Ueda | 548/178 |
| 4,218,374 | 8/1980 | Kamiya et al. | 260/239.1 |
| 4,254,029 | 3/1981 | Kaspi et al. | 260/239.1 |

FOREIGN PATENT DOCUMENTS

2704712 8/1977 Fed. Rep. of Germany.
48-53387 9/1973 Japan.
1409415 10/1975 United Kingdom.
1421080 1/1976 United Kingdom.

OTHER PUBLICATIONS

Cooper et al., "Accounts of Chemical Research", vol. 6, 1973, pp. 32–40.
Grant et al., "J. Chem. Soc.", (6), 1965, pp. 3842–3845.

*Primary Examiner*—Donald G. Daus
*Assistant Examiner*—James H. Turnipseed
*Attorney, Agent, or Firm*—Richard R. Lloyd

[57] ABSTRACT

Penicillin sulfoxide esters are reacted with an isocyanate to produce the corresponding (substituted)-2-carbamoyloxymethylpenam, the corresponding (substituted)-3-carbamoyloxycepham or the corresponding 3-methylcephem. The 6- or 7-side-chain of these products may be cleaved to give the corresponding 6-amino (penams) or 7-amino (cephams and cephems) compounds, and the latter may be reacylated to produce different 6-acyl-2-carbamoyloxymethyl penams, 7-acyl-3-carbamoyloxy cephams and 7-acyl-3-methylcephems. The substituent groups may be removed from the (substituted)-2-carbamoyloxypenams or the (substituted)-3-carbamoyloxycephams to give the corresponding free 2-carbamoyloxymethylpenams or 3-carbamoyloxycephams, respectively.

7 Claims, No Drawings

2-CARBAMOYLOXYMETHYL-PENICILLIN DERIVATIVES

BACKGROUND OF THE INVENTION

1. Field of the Invention

This invention relates to 2-carbamoyloxymethyl-penicillins, 3-carbamoyloxycephalosporins and desacetoxy cephalosporins, and to their preparation by reaction of a penicillin sulfoxide with an isocyanate.

2. Description of the Prior Art (A) U.S. Pat. No. 3,275,626 discloses, inter alia, the preparation of 2-acyloxymethyl penams, 3-acyloxy cephams and 3-methyl-$\Delta^3$-cephems by heating a penicillin sulfoxide in the presence of an acid, an acid anhydride, or the like. Generally, when the starting penicillin sulfoxide is reacted in its free acid or salt form the product is decarboxylated, while reaction of the starting penicillin sulfoxide in its esterified form yields a product retaining the esterified carboxyl moiety. The ester group is subsequently removed by, for example, hydrolysis or catalytic hydrogenation.

(B) U.K. Pat. No. 1,409,415 discloses a process for preparing 3-methyl-$\Delta^3$-cephems by heating with an anhydrous acid a penicillin sulfoxide having its carboxyl group protected by a group of the formula

 (a)

in which $R_4$ and $R_5$ are the same or different and represent, inter alia, (lower)alkyl, cycloalkyl, phenyl, phenyl(lower)alkyl, (lower)alkoxy, (lower)alkylthio, phenoxy, phenyl(lower)alkoxy, halogen, or a 6-substituted aminopenicillanic sulfoxide-3-carbonyloxy group, or $R^4$ and $R^5$ taken together with $M_1$ represent the residue of a ring system, and $M_1$ is a boron, aluminum or phosphorus atom; a group of the formula

 (b)

in which $R_4$, $R_5$ and $R_6$ are as described above for $R_4$ and $R_5$, or $R_4$ and $R_5$ taken together with $M_2$ represent the residue of a ring system, or $R_4$ and $R_5$ together represent oxygen (=O) or sulfur (=S), and $M_2$ is silicon, sulfur, germanium or tin, or a carbon atom when $R_4$ and $R_5$ together represent oxygen or sulfur; a group of the general formula

 (c)

in which $R_4$ and $R_5$ are as described above and $R_7$ and $R_8$ are each halogen or a 6-substituted aminopenicillanic sulfoxide-3-carbonyloxy group, or $R_7$ and $R_8$ taken together with $M_3$ represent the residue of a ring system, or $R_7$ and $R_8$ together represent oxygen (=O) or sulfur (=S), and $M_3$ represents phosphorus or tungsten; a group of the general formula

 (d)

in which $R_9$ is (lower)alkyl, cycloalkyl, phenyl, phenyl(lower)alkyl, (lower)alkoxy, (lower)alkylthio, phenoxy or phenyl(lower)alkoxy, and $M_4$ represents sulfur; or

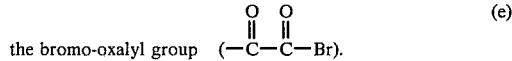 (e)

The reaction is run under anhydrous conditions in the presence of silyl compounds which are capable of rapid reaction with the water formed during the ring enlargement reaction and which form either neutral or basic compounds upon hydrolysis. In a preferred embodiment the reaction is conducted in the presence of an excess of a nitrogen containing base. The carboxyl protecting group is subsequently removed by simple hydrolysis.

(C) U.K. Pat. No. 1,421,080 discloses a process for the preparation of compounds of the formula

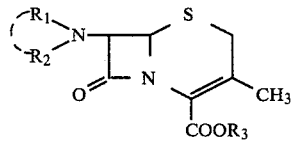

in which either $R_1$ is a hydrogen atom and $R_2$ is a phenacetyl, phenoxyacetyl, trityl, optionally protected α-aminophenacetyl radical (which may contain one or more nuclear substitutents selected from hydroxyl, alkoxy, alkyl-mercapto and halogen radicals), thienylacetyl or tert.-butoxycarbonyl radical; or $R_1$ and $R_2$ form, together with the nitrogen atom to which they are attached, a phthalimido or succinimido group; and $R_3$ is a benzyl, methoxybenzyl, nitrobenzyl, diphenylmethyl, trityl, β,β,β-trichloroethyl, cyanomethyl, 9-fluorenyl, tert.-butyl phenacyl, chlorophenacyl, bromophenacyl, nitrophenacyl, phenylphenacyl, alkoxyphenacyl, or trimethylsilyl radical; in which process a 6-acylaminopenicillanic acid ester of the general formula:

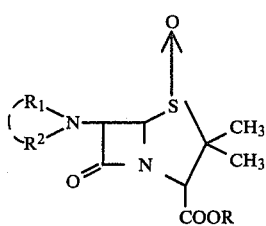

(in which $R_1$, $R_2$ and $R_3$ are as defined above) is heated to 60°–150° C. in the presence as a catalyst of a phenol of the general formula:

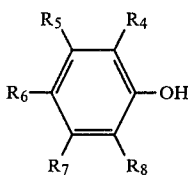

in which $R_4$, $R_5$, $R_6$, $R_7$ and $R_8$ are identical or different radicals selected from hydrogen, nitro, nitrile and halogen radicals, alkyl and haloalkyl radicals, carbalkoxy radicals, alkylcarbonyl radicals, alkylsulphonyl radicals, benzoyl, phenylsulphonyl and carbophenoxy radicals, and phenyl radicals optionally carrying one or more substituents selected from the radicals given therein as possible meanings for $R_4$–$R_8$; provided that in the general formula only one of $R_4$–$R_8$ can be a halogen atom and not more than two of $R_4$–$R_8$ can be hydrogen atoms.

(D) U.S. Pat. No. 4,010,156 discloses a process for preparing 3-halo-3-methylcepham derivatives of the formula

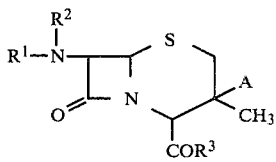

in which $R^1$ is hydrogen or an organic acyl radical; $R^2$ is hydrogen or, taken together with $R^1$-N, may represent phthalimido or

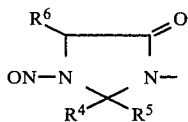

in which $R^4$ and $R^5$ are hydrogen or (lower)alkyl and $R^6$ is phenyl or 1,4-cyclohexadienyl; $R^3$ is hydroxy, (lower)alkoxy, 2,2,2-trichloroethoxy, aryloxy, aralkoxy, alkoxyaralkoxy, mono- or di-(lower)alkylamino, arylamino saccharimido, phthalimido or OM in which M is an alkali metal cation, an alkaline earth metal cation or the ammonium cation; and A is chloro, bromo or iodo. The compounds are prepared by heating the corresponding penicillin sulfoxide of the formula

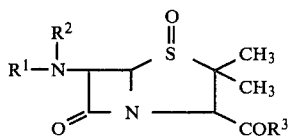

in which $R^1$, $R^2$ and $R^3$ are as defined above in a polyhaloalkane solvent in the presence of an equimolar amount of any of certain specified quaternary ammonium salt catalysts. The 3-halo compound is then dehydrohalogenated to form the corresponding cephem compound. Alternatively, the cephem compound may be produced in one step from the penicillin sulfoxide by utilizing a basic catalyst such as pyridine instead of the quaternary ammonium salt catalyst.

(E) U.S. Pat. No. 3,997,533 discloses a process for converting penicillin sulfoxide esters to the corresponding 3-methyl-$\Delta^3$-cephem compound by heating in the presence of a heavy metal salt catalyst of the formula $$Me(R''SO_3)_n$$

wherein Me is copper, silver, gold, zinc, cadmium, mercury, thallium, tin, lead, iron, cobalt or nickel; R'' is (lower)alkyl, fluoro(lower)alkyl or substituted or unsubstituted phenyl or naphthyl; and n is 1–3 depending on the valence of Me.

(F) Japanese Patent Publication No. 50-53387 discloses a process for preparing compounds of the formula

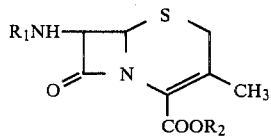

in which $R_1$ is hydrogen, acyl or substituted silyl and $R_2$ is hydrogen, alkyl, aryl, aralkyl or substituted silyl, by heating a penicillin sulfoxide of the formula

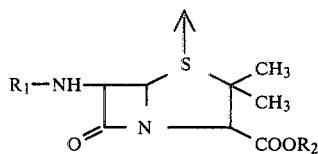

in which $R_1$ and $R_2$ are as described above, in a non-reactive organic solvent, with 1–5 equivalents of an isocyanate of the formula $$R_3-(NCO)_n$$

in which $R_3$ is alkyl, aryl, aralkyl, alkylene or arylene and n is 1–3. It is stated that the reaction is accelerated by the addition of 0.1 mole of pyridine, quinoline or isoquinoline per mole of penicillin sulfoxide. Specifically mentioned isocyanates are phenyl isocyanate, toluene-2,4-diisocyanate, methyl isocyanate, isobutyl isocyanate and hexamethylene diisocyanate. The patent does not teach the use of acyl isocyanates, substituted sulfonyl, sulfinyl or sulfenyl isocyanates, or substituted metal or non-metal isocyanates.

It has been our finding with the above reaction that phenyl isocyanate is not sufficiently reactive to transform a penicillin sulfoxide ester unless a base is present. The transformation of penicillin sulfoxides to cephalosporins is accompanied by the elimination of a mole of water for every mole of 3-methylcephalosporin produced. This water, when scavenged by an alkyl or aryl isocyanate (as in the above patent), gives an alkyl or aryl amine, which in turn may be scavenged by excess isocyanates or by the $\beta$-lactam. The latter unwanted reaction may account for poor yields in the above process for ring expansion. Because of this, the reaction of alkyl or aryl isocyanates with penicillin sulfoxides is of no commercial interest. A further drawback of the alkyl and aryl isocyanates is their extreme toxicity. Isocyanates which do not give alkyl or aryl amines, or their derivatives, on hydrolysis were considered by us to offer new prospects not compromised by the production of unwanted side products. Activated isocyanates such as acyl isocyanates, substituted sulfonyl, sulfinyl or sulfenyl isocyanates, and substituted metal and nonmetal isocyanates offer a potential which has hitherto been unexamined.

(G) Various excellent reviews of prior art processes for rearrangements and/or ring expansion of penicillin sulfoxides are available. See, for example, R. D. G. Cooper, et al., Accounts of Chemical Research, 6, 32 (1973) and Chapter 5, entitled "Rearrangements of Cephalosporins and Penicillins", in the book Cephalosporins and Penicillins, E. H. Flynn, ed., Academic Press, New York, 1972.

(H) W. German OLS No. 2,704,712 discloses, inter alia the reaction of 3-hydroxymethyl $\Delta^3$-cephems with certain isocyanates to produce the corresponding substituted 3-carbamoyloxymethyl $\Delta^3$-cephems, with optional removal of the substituent group. A specific example was as follows ($R^1$=tritylamino):

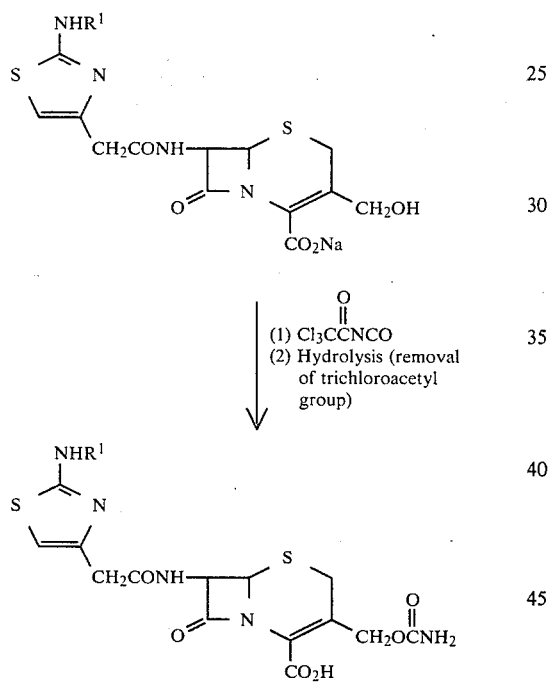

DETAILED DESCRIPTION

This invention relates to $\beta$-lactam antibiotics. More specifically, it relates to the reaction of a penicillin sulfoxide with an isocyanate to produce the corresponding 2-carbamoyloxymethylpenam, the corresponding 3-carbamoyloxycepham or the corresponding 3-methylcephem. In another aspect, this invention relates to the cleavage of the above products to produce the corresponding compounds having a free amino group in the 6-position (penams) or 7-position (cephams and cephems), and to the acylation of the free amino groups of these latter compounds to produce still different 6-acyl-2-carbamoyloxymethylpenams, 7-acyl-3-carbamoyloxycephams and 7-acyl-3-methylcephems.

The reactions may be better visualized by reference to the following general reaction schemes.

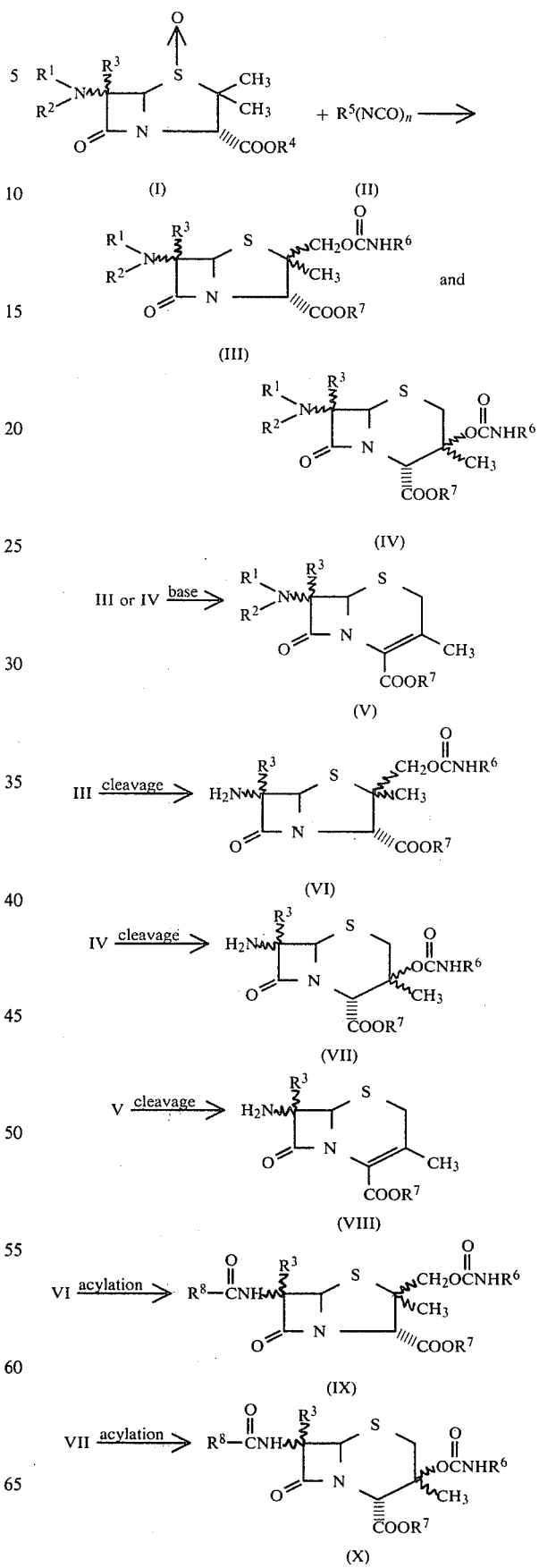

VIII <u>acylation</u> → 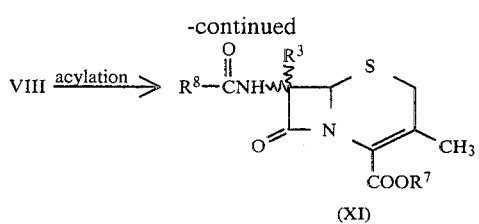
(XI)

In the above general reaction schemes,
R¹ is hydrogen and
R² is an amino-blocking group or a conventional acyl group known in the penicillin or cephalosporin art, or
R¹ and R², taken together with the nitrogen to which they are attached, may form a phthalimido group, a succinimido group or a group of the formula

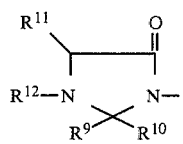

in which $R^9$ and $R^{10}$ are (lower)alkyl, $R^{11}$ is 1,4-cyclohexadienyl, substituted or unsubstituted phenyl, or a substituted or unsubstituted heterocyclic group containing one or more hetero atoms such as sulfur, oxygen and/or nitrogen, e.g. thienyl, furyl, tetrazolyl, thiazolyl or thiadiazolyl; and $R^{12}$ is hydrogen, an aldehydo group or a nitroso group;
$R^3$ is hydrogen, (lower)alkoxy, (lower)alkylthio or

in which $R^{13}$ is substituted or unsubstituted (lower)alkyl or aryl;
—COOR⁴ is a protected carboxyl group or a derivative of a carboxyl group;
$R^5$ is an acyl group, a thioacyl group, a substituted sulfonyl, sulfinyl or sulfenyl group, or a substituted metal or non-metal atom having a valence of from 2 to 5;
n is an integer of from 1 to 4;
$R^6$ is hydrogen, is the same as $R^5$, or is

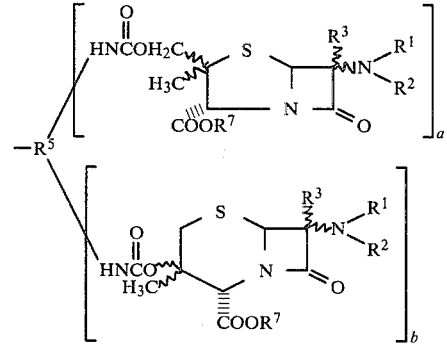
(XII)

in which R¹, R², R³ and R⁷ are as defined above, and a and b are the same or different and represent an integer from 0 to n−1, wherein n is as defined above, provided that the sum of a and b is not greater than n−1;
$R^7$ is hydrogen or the same as $R^4$; and

is a conventional acyl group known in the penicillin and cephalosporin art.

The isocyanates of Formula II, above, include, for example, those of the following formulae.

(a) W₂—M₂—NCO in which M₂ is a divalent metal or non-metal atom (and preferably sulfur or selenium) and W₂ is a substituted or unsubstituted alkyl, aryl or aralkyl group, or an isocyanate group. Examples of isocyanates falling within this class are trichloromethylsulfenyl isocyanate, dichloromethylsulfenyl isocyanate, trifluoromethylsulfenyl isocyanate, difluoromethylsulfenyl isocyanate, 2,4-dinitrophenylsulfenyl isocyanate, sulfenyl diisocyanate, selenium diisocyanate, chloromethyl selenium isocyanate, dichloromethyl selenium isocyanate trichloromethyl selenium isocyanate, mono-, di- or trifluoromethyl selenium isocyanate, and the like.

(b)

in which M₃ is a trivalent metal or non-metal atom, W₃ and X₃ are the same or different and represent a substituted or unsubstituted (lower)alkyl, aryl, ar(lower)alkyl, cycloalkyl, (lower)alkoxy, aryloxy, ar(lower)alkoxy, (lower)alkylthio, or ar(lower)alkylthio group, or an isocyanate group; or W₃ and X₃, taken together with M₃, represent a ring system. Examples of isocyanates falling within this class are phosphorous triisocyanate, boron triisocyanate, antimony triisocyanate, aluminum triisocyanate, (C₄H₉)₂BNCO, (C₂H₅)₂AlNCO, C₄H₉B(NCO)₂, C₂H₅Al(NCO)₂, (C₆H₅)₂PNCO, (C₂H₅O)₂BNCO, (C₆H₅CH₂O)₂PNCO, (C₂H₅S)₂PNCO, (CH₃O)₂PNCO, ClCH₂CH₂OP(NCO)₂,

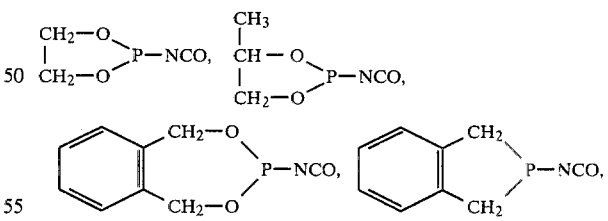

and the like.

(c)

in which M₄ is a tetravalent metal or non-metal atom, W₄, X₄ and Y₄ are the same or different and represent a substituted or unsubstituted (lower)alkyl, aryl, ar(lower)alkyl, cycloalkyl, (lower)alkoxy, aryloxy, ar(lower)alkoxy, (lower)alkylthio, or ar(lower)alkylthio group, or an isocyanate group; or W₄ and X₄, taken together with M₄, represent a ring system; or W₄, X₄ and Y₄, taken together with M₄, represent a ring system other than phenyl or substituted phenyl; or W₄ and X₄, taken together, represent =O, =S or =NW₄. Examples of isocyanates within this class are:

(1) acyl isocyanates and thioacyl isocyanates such as acetyl isocyanate, mono-, di- or trichloroacetyl isocyanate, mono-, di- or trifluoroacetyl isocyanate, propionyl and butyryl isocyanates and their chlorinated or fluorinated analogs, phenylacetyl isocyanate, cyanoacetyl isocyanate, benzoyl isocyanate, p-nitrobenzoyl isocyanate, 2,4-dinitrobenzoyl isocyanate, benzyloxycarbonyl isocyanate, p-nitrobenzyloxycarbonyl isocyanate, methoxycarbonyl isocyanate, chloromethoxycarbonyl isocyanate, carbonyl diisocyanate, cyanocarbonyl isocyanate, and the like, as well as their thio analogs, e.g. trichlorothioacetyl isocyanate, chloromethoxythiocarbonyl isocyanate, and the like;

(2) sulfinyl isocyanates of the formula

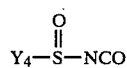

in which Y₄ is as defined above;

(3) metal and non-metal tetraisocyanates such as Sn(NCO)₄, Se(NCO)₄, Ti(NCO)₄, Ge(NCO)₄, Si(NCO)₄, and the like;

(4) substituted metal and non-metal isocyanates of the formula

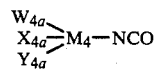

in which M₄ is as defined above and W₄ₐ, X₄ₐ and Y₄ₐ are the same or different and represent substituted or unsubstituted (lower)alkyl, (lower)alkoxy or (lower)alkylthio; or W₄ₐ or both W₄ₐ and X₄ₐ, may be an isocyanate group; or W₄ₐ and X₄ₐ, taken together with M₄, may represent a ring system. Examples of isocyanates falling within this class are (CH₃)₃SnNCO, (CH₃)₃SbNCO, (CH₃)₃GeNCO, (CH₃)₃TiNCO, (CH₃)₂Sn(NCO)₂, (CH₃)₂Sb(NCO)₂, CH₃Ti(NCO)₃, CH₃Ge(NCO)₃, (C₂H₅O)₃SnNCO, (C₂H₅O)₃SbNCO, (C₂H₅S)₃TiNCO, (C₂H₅S)₃GeNCO, (ClC₂H₄)₃SbNCO,

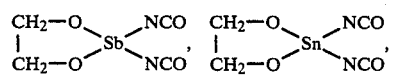

and the like;

(5) silyl isocyanates of the formula

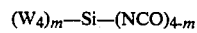

in which W₄ is as described above and m is an integer of from 1 to 3. Examples of isocyanates falling within this class include trimethylsilyl isocyanate, dimethylsilyl diisocyanate, methylsilyl triisocyanate, trimethoxysilyl isocyanate, triethoxysilyl isocyanate, triethylsilyl isocyanate, diphenylsilyl diisocyanate, dibenzyloxy diisocyanate, triphenylsilyl isocyanate, tribenzylsilyl isocyanate, (ClC₂H₄)₃SiNCO, (ClC₂H₄O)₂Si(NCO)₂, (C₆H₅O)₂Si(NCO)₂,

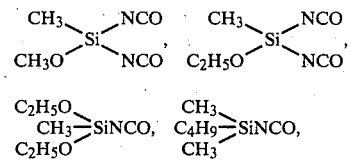

and the like; and (6) ring compounds of the formula

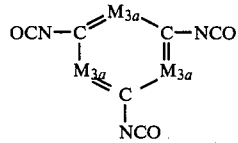

in which M₃ₐ is nitrogen, boron, phosphorus or antimony.

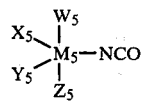                                                      (d)

in which M₅ is a pentavalent metal or non-metal atom and W₅, X₅, Y₅ and Z₅ are the same or different and represent a substituted or unsubstituted (lower)alkyl, aryl, aryloxy, (lower)alkoxy, or (lower)alkylthio group, or an isocyanate group; or W₅ and X₅, taken together with M₅, represent a ring system; or W₅ and X₅, taken together, represent =O or =S. Examples of isocyanates within this class are (C₄H₉)₃Sb(NCO)₂, (CH₃)₄SbNCO, (ClC₂H₄)₃Sb(NCO)₂,

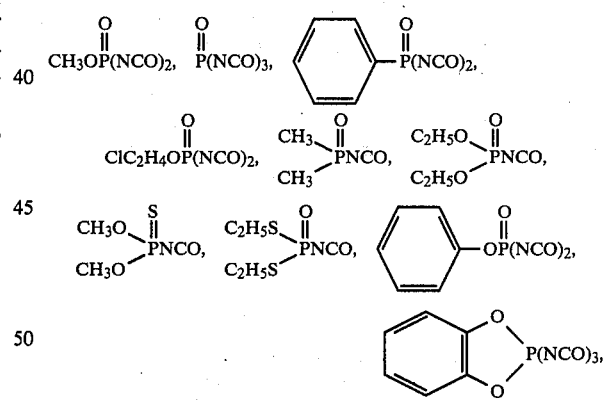

and the like.

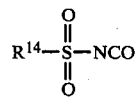                                                      (e)

in which R¹⁴ is a substituted or unsubstituted (lower)alkyl, aryl, ar(lower)alkyl, cycloalkyl, (lower)alkoxy, aryloxy, ar(lower)alkoxy, (lower)alkylthio, or ar(lower)alkylthio group, or an isocyanate group. Examples of isocyanates falling within this class are methylsulfonyl isocyanate, chloromethylsulfonyl isocyanate, phenylsulfonyl isocyanate, p-nitrophenylsulfonyl isocyanate, 2,4-dinitrophenylsulfonyl isocyanate, toluenesulfonyl isocyanate, phenoxysulfonyl isocyanate, benzyloxysulfonyl isocyanate, ethoxysulfonyl isocyanate, ethylthiosulfonyl isocyanate, sulfonyl diisocyanate, and the like.

In one preferred embodiment of the invention, in the penicillin sulfoxide ester starting material of Formula I, $R^1$ and $R^2$, taken together with the nitrogen to which they are attached, may form a phthalimido group, a succinimido group or a group of the formula

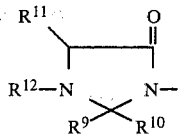

in which $R^9$ and $R^{10}$ are (lower)alkyl, $R^{11}$ is 1,4-cyclohexadienyl, substituted or unsubstituted phenyl, or a substituted or unsubstituted heterocyclic group containing one or more hetero atoms such as sulfur, oxygen and/or nitrogen, e.g. thienyl, furyl, tetrazolyl, thiazolyl or thiadiazolyl, and $R^{12}$ is hydrogen, an aldehydo group or a nitroso group.

In a more preferred embodiment $R^1$ and $R^2$, taken together with the nitrogen to which they are attached, form a group of the formula

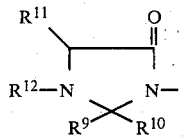

in which $R^9$ and $R^{10}$ are as defined above (but preferably are each methyl), $R^{12}$ is as defined above (but preferably is hydrogen, and $R^{11}$ is as defined above (but preferably is 1,4-cyclohexadienyl, phenyl, p-hydroxyphenyl, thienyl, furyl, tetrazolyl, thiazolyl or thiadiazolyl). Most preferably, $R^{11}$ is phenyl or p-hydroxyphenyl. It is also preferred that $R^6$ be hydrogen.

In another preferred embodiment of the invention, in the penicillin sulfoxide ester starting material of Formula I, $R^1$ is hydrogen and $R^2$ is an acyl group of the formula

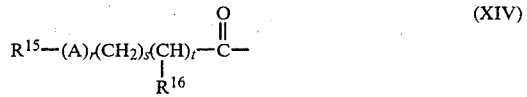 (XIV)

in which r is 0 or 1, s is an integer of from 0 to 6, t is 0 or 1, A is oxygen or sulfur, $R^{16}$ is amino, substituted amino, acylamino, hydroxy, azido, halogen, carboxy, carbamoyl, guanidino, sulfo, sulfamino, phosphono, acyloxy, tetrazolyl, carboalkoxy, or the like, and $R^{15}$ is hydrogen, or a substituted or unsubstituted alkyl, aryl, aralkyl, cycloalkyl, heterocyclyl or heterocyclylalkyl group.

In a more preferred embodiment, the acyl group of Formula XIV has the structure

 (XV)

in which $R^{15}$ is as defined above. Group $R^{15}$ may be unsubstituted or may be substituted by such groups as OH, SH, SR (where R is alkyl or aryl), alkyl, alkoxy, aryl, halo, cyano, carboxy, nitro, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, guanidinoalkyl, or the like. Examples of suitable acyl groups of Formula XV are those in which $R^{15}$ is benzyl, p-hydroxybenzyl, 4-amino-4-carboxybutyl, methyl, cyanomethyl, n-amyl, n-heptyl, ethyl, propyl, isopropyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, 2- or 3-(5-methylthienyl)methyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4-guanidinomethylbenzyl, 4-quanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolymethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl, cyclopentyl, cyclohexyl, cycloheptyl cyclohexylmethyl, cyclohexylpropyl, dihydrobenzyl, dihydrophenylmethyl, tolylmethyl, xylylmethyl, tetrahydronaphthylmethyl, piperazinylmethyl, pyrrolidinylmethyl, benzothiazolylmethyl, benzoxazolylmethyl, and 1H (or 2H)-tetrazolylmethyl.

In another more preferred embodiment, the acyl group of Formula XIV has the structure

 (XVI)

wherein $R^{15}$, A and s are as defined above. Examples of suitable groups of the formula $R^{15}A(CH_2)_s$— include methoxymethyl, methylthiomethyl, cyclohexylthiomethyl, cyclohexyloxymethyl, dihydrophenoxymethyl, dihydrophenylthiomethyl, cyclopentyloxy, cyclohexyloxy, dihydrophenoxy, benzyloxy, xylyloxy, tolyloxy, naphthoxy, phenylthiomethyl, butylmercaptomethyl, allylthiomethyl, 2-furyloxy, 8-quinolyloxy, pyridylmethoxy, trichloroethoxy, 1-cyclopropylethoxy, p-nitrobenzyloxy, o-chlorobenzyloxy, o-nitrobenzyloxy, p-methoxybenzyloxy, 3,4-dimethoxybenzyloxy, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxy)phenylthiomethyl, p-(carboxymethyl)phenylthiomethyl, p-(carboxymethyl)phenylthiomethyl, 2-pyrimidinylthiomethyl, phenethylthiomethyl and 1-(5,6,7,8-tetrahydronaphthyl)oxomethyl.

In another more preferred embodiment, the acyl group of Formula XIV has the structure

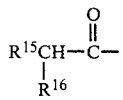
 (XVII)

wherein $R^{15}$ and $R^{16}$ are as defined above. Examples of suitable groups of the formula

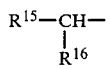

include α-aminobenzyl, α-amino-2-thienyl, α-methylaminobenzyl, α-amino-methylmercaptopropyl, α-amino-3- or 4-chlorobenzyl, α-amino-3 or 4-hydroxybenzyl, α-amino-2,4-dichlorobenzyl, α-amino-3,4-dichlorobenzyl, β(−)-α-hydroxybenzyl, α-carboxybenzyl, α-amino-3-thienyl, α-amino-2-thienyl, D-(−)-α-amino-3-chloro-4-hydroxybenzyl, D(−)-α-amino-3-thienyl, 1-aminocyclohexyl, α-(5-tetrazolyl)benzyl, 2-(α-carboxy)thienylmethyl, 3-(α-carboxy)furylmethyl, α-sulfaminobenzyl, α-sulfamino-3-thienyl, α-(N-methylsulfamino)benzyl, D(−)-α-guanidino-2-thienyl, D(−)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-oxadiazolyl)carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)-hydroxymethyl, 2-(5-chlorothienyl)carboxymethyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, and α-phosphonobenzyl.

If the acyl group contains a functional group, such as amino, hydroxy, mercapto or carboxy, the functional group may be protected with an appropriate protective group. Because the acyl side-chain may subsequently be cleaved to produce the free amino compound (which may, if desired, be re-acylated with a different side-chain), it is not always necessary to protect reactive substituent groups in the side-chain.

Suitable protective groups for the amino radical include any of the conventional protective groups such as those acyl groups which can easily be split off (e.g. trichloroethoxycarbonyl, benzyloxycarbonyl, p-toluenesulfonyl, p-nitrobenzyloxycarbonyl, o-chlorobenzyloxycarbonyl, o-nitrophenylsulfenyl, chloroacetyl, trifluoroacetyl, formyl, tert-butoxycarbonyl, p-methoxybenzyloxycarbonyl, 3,4-dimethoxybenzyloxycarbonyl, 4-phenylazobenzyloxycarbonyl, 4-(4-methoxyphenylazo)benzyloxycarbonyl, pyridine-1-oxide-2-methoxy-carbonyl, 2-pyridylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl or 8-quinolyloxycarbonyl), or other radicals which can easily be split off (e.g. trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene, or mono- or bis-trialkylsilyl). Other conventional amino protecting groups such as those described in "Protective Groups in Organic Chemistry," J. F. W. McOmie, Ed., Plenum Press, New York, New York, 1973 Chapter 2, shall be recognized as suitable.

Suitable protective groups for the hydroxy or mercapto groups include any of the conventional protective groups for hydroxy or mercapto groups such as the acyl groups which can be easily split off (e.g. benzyloxycarbonyl, 4-nitrobenzyloxycarbonyl, 4-methoxybenzyloxycarbonyl, 3,4-dimethoxybenzyloxycarbonyl, 4-phenylazobenzyloxycarbonyl, 4-(4-methoxyphenylazo)benzyloxycarbonyl, tert-butoxycarbonyl, 1,1-dimethylpropoxycarbonyl, isopropoxycarbonyl, 1-adamantyloxycarbonyl, 1-cyclopropylethoxycarbonyl, 8-quinolylethoxycarbonyl, 2,2,2-trichloroethoxycarbonyl, 3-iodopropoxycarbonyl, 2-furfuryloxycarbonyl, 8-quinolyloxycarbonyl and trifluoroacetyl) and those protecting groups other than acyl groups which can be easily split off, such as benzyl, trityl, methoxymethyl, 2-nitrophenylthio and 2,4-dinitrophenylthio. Other conventional hydroxy and mercapto protecting groups, including those described in "Protective Groups in Organic Chemistry", supra, Chapters 3 and 7, shall be considered as suitable.

The protective group for the carboxy group may be any of those conventional protective groups used for protecting a carboxy group, e.g. an ester group such as methyl, ethyl, propyl, isopropyl, tert-butyl, butyl, benzyl, diphenylmethyl, triphenylmethyl, p-nitrobenzyl, p-methoxybenzyl, benzoylmethyl, acetylmethyl, p-nitrobenzoylmethyl, p-chlorobenzoylmethyl, p-methanesulfonylbenzoylmethyl, phthalimidomethyl, trichloroethyl, 1,1-dimethyl-2-propynyl, acetoxymethyl, propionyloxymethyl, pivaloyloxymethyl, 1,1-dimethylpropyl, 1,1-dimethyl-2-propenyl, 3-methyl-3-butenyl, succinimidomethyl, 1-cyclopropylethyl, 3,5-di(tert)butyl-4-hydroxybenzyl, methylsulfenylmethyl, phenylsulfenylmethyl, methylthiomethyl, phenylthiomethyl, dimethylaminomethyl, 2-methoxquinoline-1-oxide, 2-methylpyridine-1-oxide, chlorooxalyl or di(p-methoxyphenyl)methyl ester, the silyl ester groups derived from a silyl compound such as dimethyldichlorosilane (which have been reported in U.S. Pat. No. 3,944,545, in Japanese Patent Application No. 7332/1971 laid open to public inspection under No. 7073/1971 and in Netherlands Patent Application laid open to public inspection under No. 7,105,259), and metallic or non-metallic derivatives of the carboxy group derived from such compounds as boron trichloride, $(C_2H_5)_2AlCl$, $(CH_3O)_2PCl$ and the like which have been disclosed in U.K. Pat. No. 1,409,415. Other known conventional carboxyl protecting groups such as those described in "Protective Groups in Organic Chemistry", supra, Chapter 5, shall be recognized as suitable.

In compound I, above, —COOR$^4$ is defined as a protected carboxyl group or a derivative of a carboxyl group. Suitable carboxyl-protecting groups are well known in the art, and include those listed above for protecting carboxyl substituents on the acyl side-chain. R$^4$ also may be a metallic or non-metallic derivative such as described above for protecting carboxyl substitutents. The group —COOR$^4$ preferably is (1) an ester: a silyl ester such as referred to above, an alkyl or alkenyl (e.g., methyl, ethyl, propyl, isopropyl, butyl, tert-butyl, cyclohexyl, cycloheptyl, vinyl, 1-propenyl, 2-propenyl or 3-butenyl) ester, aryl (e.g., phenyl xylyl, tolyl or naphthyl) ester, aralkyl (e.g., benzyl or diphenylmethyl) ester, or an ester wherein one of the carbon atoms of the alkyl group is replaced with a nitrogen, sulphur or oxygen atom, or by a carbonyl group, such as methoxymethyl ester, ethoxymethyl ester, methylthioethyl ester, methylthiomethyl ester, dimethylaminoethyl ester, diethylaminoethyl ester, phenoxymethyl ester, phenylthiomethyl ester, methylsulfenylmethyl ester, phenylsulfenylmethyl ester, benzoylmethyl ester or toluoylmethyl ester, or an ester containing one or more appropriate substituents (e.g., halogen, alkoxy, alkanesulfonyl or phenylazo) such as chloromethyl ester, bromomethyl ester, trichloroethyl ester, cyanomethyl ester, p-nitrophenyl ester, 2,4,5-trichlorophenyl ester, 2,4,6-trichlorophenyl ester, pentachlorophenyl ester, p-methylsulfonylphenyl ester, 4-phenylazophenyl ester, 2,4-dinitrophenyl ester, p-chlorobenzyl ester, o-nitrobenzyl ester, p-methoxybenzyl ester, p-nitrobenzyl ester, 3,4,5-trimethoxybenzyl ester, bis(p-methoxyphenyl)methyl ester, pentachlorobenzyl ester, trichlorobenzyl ester, 3,5-di(tert)butyl-4-hydroxybenzyl ester, p-nitrophenylthiomethyl ester, p-nitrobenzoylmethyl ester or p-chlorobenzoylmethyl ester, or an ester formed from a thioalcohol, a substituted thioalcohol, N-hydroxysuccinimide, N-hydroxyphthalimide, tetrahydrofuran, 1-cyclopropylethanol, 1-phenyl-3-methyl-5-pyrazolone, 3-hydroxypyridine, 2-hydroxymethylpyridine-1-oxide, 1-hydroxy-2(1H)-pyridine, dimethylhydroxyamine, diethylhydroxyamine, glycolamide, 8-hydroxyquinoline, 2-hydroxymethylquinoline-1-oxide, methoxyacetylene, ethoxyacetylene, tert-butylethynyldimethylamine, tert-butylethynyldiethylamine, ethylethynyldiethylamine or 2-ethyl-5-(3-sulfophenyl)isoxazolium hydroxide inner salt; or (2) an acid amide: an N-alkyl amide (e.g., N-methyl acid amide or N-ethyl acid amide), N,N-dialkyl acid amide (e.g., N,N-dimethyl acid amide, N,N-diethyl acid amide or N-methyl-N-ethyl acid amide), or an acid amide with imidazole, benzotriazole, a 4-substituted imidazole or a protected tetrazole.

Other known conventional carboxy protecting groups such as those described in "Protective Groups in Organic Chemistry", supra, Chapter 5, shall be recognized as suitable.

The reaction of the penicillin sulfoxide (I) with the isocyanate (II) is conducted in an inert organic solvent such as dioxane, toluene, xylene, benzene, tetrahydrofuran, methyl isobutyl ketone, 1,2-dichloroethane, methyl chloroform or the like. The reaction may, if desired, be conducted in excess isocyanate as the solvent. Dioxane is a preferred solvent.

The reaction may be conducted over a wide temperature range, e.g. up to about 200°, preferably from about 70° to about 140° and most preferably from about 90° to about 115°. It is most convenient to conduct the reaction at the reflux temperature of a suitably selected solvent.

The reaction time is not critical and may range from 1 hour to 24 hours, or more, depending on the particular reactants, reaction temperature, etc.. In general, we prefer to conduct the reaction for from about 1 to about 10 hours, and typically from about 3 to about 7 hours.

The penicillin sulfoxide (I) is reacted with at least one equivalent of the isocyanate (II) and preferably with an excess thereof. Up to about 5 equivalents, or more, of isocyanate may be utilized, but no advantage is obtained by using greater amounts. The isocyanate aids in maintaining an anhydrous reaction medium by scavenging any free water which may be present. We prefer to use from about 2 to 4 equivalents of the isocyanate, and most preferably about 3 equivalents of the isocyanate, per equivalent of the penicillin sulfoxide.

If the reaction of the penicillin sulfoxide (I) and the isocyanate (II) is conducted in the absence of a base the product is primarily a mixture of the penam (III) and the cepham (IV), along with a small amount of the cephem (V). The ratio of the penam and cepham in the product may be varied by the use of different isocyanates. Thus, for example, when the p-nitrobenzyl ester of penicillin V sulfoxide is reacted in dioxane with silicon tetraisocyanate, the product usually consists of 95–98% of the penam and traces of the cepham. However, the reaction of the p-nitrobenzyl ester of penicillin V sulfoxide in dioxane with trichloroacetyl isocyanate gives a product which typically is 30–35% penam, 60–65% cepham and about 5% cephem. The product mixture may readily be separated into its components by chromatography, e.g. on silica gel.

Penam (III) and/or cephem (IV) may be converted to cephem (V) by treatment with base, as shown in the general reaction scheme, above. Alternatively, if the cephem (V) is the desired product, the penicillin sulfoxide (I) may be reacted with the isocyanate (II) in the presence of a base to give the cephem (V) directly. When preparing the cephem directly in this manner, we have found that highest yields of the cephem are obtained if a source of bromide ions is also added to the reaction mixture.

When converting penam (III) and/or cepham (IV) to cephem (V) by treatment with base, one may use any organic or inorganic base. The reaction may be conducted in an organic solvent by using a base which is soluble therein or by using a two-phase aqueous-organic solvent system wherein the base is water soluble.

When utilizing a two-phase system for base treatment of the penam and/or cepham, one may utilize any of the usual water-soluble bases, e.g. NaOH, KOH, $K_2CO_3$, $Na_2CO_3$, $NaHCO_3$, $KHCO_3$, an alkaline phosphate buffer, or the like. When the base treatment is conducted in an organic solvent, one may use any of the usual organic-soluble bases, e.g. a tertiary amine such as triethylamine, pyridine, quinoline, isoquinoline, lutidine, tetramethylguanidine, or the like. We have found that some bases such as $K_2CO_3$, which are generally considered to be insoluble in organic solvents, appear to have sufficient solubility in certain organic solvents such as dioxane to be utilized in such systems.

Thus, the penam (III) and/or cepham (IV) (either as isolated products or as the crude reaction mixture) may be converted to the corresponding cephem (V) by adjusting a solution thereof to an alkaline pH and maintaining it at an alkaline pH for from about 15 minutes to 24 hours, depending on the temperature, base, particular reactants and solvent system. The temperature is not critical. We find that 0°–40° is a convenient range and that 0°–25° is preferred. Higher temperatures may be used but normally decrease the yield of desired product, while lower temperatures require excessively long reaction times.

The base utilized to convert the penam and/or cepham to the cephem need not be added in a stoichiometric amount, as this is merely a catalyst. We have utilized from about 5 to about 150 mole percent of base and prefer to use from about 20 to about 50 mole percent. A greater amount of base may be utilized but normally does not increase the yield. The use of less than about 5 mole percent of base usually unduly increases the reaction time and/or yield of product. The most suitable amount of base depends on the particular penam and/or cepham being treated, as well as on the particular solvent system.

As indicated above, we have found that, in the "one-step" reaction of a penicillin sulfoxide with an isocyanate in the presence of a base to produce the cephem directly, the yield of cephem is normally significantly increased by the addition of a source of bromide ions to the reaction mixture. Suitable sources of bromide ion will be apparent to those skilled in the art, and include acetyl bromide, propionyl bromide, benzoyl bromide, pyridine hydrobromide, trimethylbromosilane, thionyl bromide, boron tribromide, silicon tetrabromide, aluminum tribromide, tin tetrabromide, and the like. The amount of bromide giving the best yield of cephem will depend on the particular penicillin sulfoxide, isocyanate, base and solvent being utilized. We have found that from about 5 to about 50 mole percent of bromide is adequate while from about 10 to about 30 mole percent is usually preferred.

After reaction of the penicillin sulfoxide with the isocyanate to produce the desired penam (III), cepham (IV) or cephem (V), the latter products will still contain a protected carboxyl group, i.e. $R^7$ is initially the same as $R^4$. It is usually desired to remove the protecting group to produce the corresponding compound containing a free carboxyl group (i.e. $R^7$ is hydrogen). Removal of the carboxyl-protecting group is achieved by conventional treatment, e.g. catalytic hydrogenolysis in the case of the p-nitrobenzyl protecting group. This may be accomplished, for example, by the use of hydrogen in the presence of a catalyst such as palladium or rhodium on a carrier such as charcoal, barium sulfate or alumina. Alternative methods of removal of the protecting group include reaction with Lewis acids such as trifluoroacetic acid, formic acid or zinc bromide in benzene (the reaction with Lewis acids may be facilitated by the addition of a nucleophile such as anisole), or by reduction with agents such as zinc/acetic acid or zinc/formic acid, or by reaction with nucleophiles such as those containing a nucleophilic oxygen or sulfur atom, e.g. alcohols, mercaptans or water.

The side chains of penam (III), cepham (IV) and cephem (V) may, if desired, be cleaved to give the free 6-amino compound (penams) or 7-amino compound (cephams and cephems). Cleavage may be effected by means of enzymes or by chemical hydrolysis or hydrogenolysis. If the side chain is to be cleaved, such cleavage preferably is conducted prior to removal of the carboxyl-protecting group. In the chemical hydrolysis of the side chain, the penam, cepham or cephem is first converted to an imino halide by reaction with a halogenating agent such as phosphorus pentachloride, phosphorus oxychloride, phosgene, thionyl chloride, oxalyl chloride or p-toluenesulfonyl chloride (and preferably phosphorus pentachloride or phosphorus oxychloride) in the presence of an acid binding agent. The reaction is conducted in an inert organic solvent such as diethyl ether, nitromethane or a halogenated hydrocarbon (methylene chloride and chloroform are the preferred solvents). It is preferred to use an excess of the halogenating agent (up to about 2 moles per mole of penam, cepham or cephem) and to use from about 1.5 to about 5 moles of acid binding agent per mole of halogenating agent. Suitable acid binding agents are tertiary amines such as triethylamine, N,N-dimethylaniline, pyridine, quinoline lutidine, picoline and the like. The reaction may be conducted at a temperature of from about −60° to −10° for penams and at from about −60° to about +10° for cephams and cephems. We prefer to conduct the reaction at from about −30° to about −40°.

The imino halide prepared in the above step is then converted into an imino ether by reaction with a primary or secondary alcohol in the presence of an acid binding agent (this is usually most simply accomplished by conducting this step without isolation of the imino halide). Suitable alcohols include alkanols such as methanol, ethanol, propanol, isopropanol, butanol and isobutanol; aralkanols such as benzyl alcohol and 2-phenylethanol; cycloalkanols such as cyclohexanol; and alkanediols such as ethylene glycol and 1,6-hexanediol. The preferred alcohol is methanol. The reaction may be conducted over the same temperature range as in the formation of the imino halide, and preferably is conducted at from about −30° to about −40°.

The imino ether is then hydrolyzed to produce the free amino compound. This is most simply accomplished by quenching the solution of the imino ether with water at a temperature of from about −5° to about +10°.

Chemical cleavage of the acyl side-chain, such as described above, also will remove some or all of the substituent $R^6$ on the penam and cepham, depending on the particular nature of $R^6$, the particular halogenating agent which is utilized, the temperature at which the reaction is conducted, the particular work-up procedure, etc. Thus, with the penam having a phenoxyacetamido side-chain and $R^6$ substituent which is trichloroacetyl, $PCl_5$ mediated cleavage followed by work-up in methanol with a bicarbonate will remove both groups. In such cases (where two acyl groups are being removed) one should utilize about twice the amount of halogenating agent and alcohol referred to above. In those cases where little or no $R^6$ group is removed during side-chain cleavage, the amount of halogenating agent and alcohol should be in the range stated above. It will be appreciated by those skilled in the art that $PCl_5$ side-chain cleavage cannot be utilized on compounds III or IV wherein $R^6$ is hydrogen, since the free carbamoyl group will be destroyed. The side-chain may be removed without removing substituent $R^6$ of the penam or cepham (wherein $R^6$ is other than hydrogen) by utilizing specific halogenating agents and specific $R^6$ substituents. Similarly, one may remove the $R^6$ substituent of the penam or cepham without removing the side-chain by utilizing suitable $R^6$ substituents and methods of removal, e.g. if $R^6$ is chloroacetyl, it may be removed with thiourea, without removing the side-chain. The trichloroacetyl group may be removed by the use of sodium bicarbonate in methanol.

Cleavage of the 6- or 7-acyl side-chain in the penam (III) or cepham (IV) may be achieved by hydrogenolysis techniques when the side-chain is a group readily removed by such techniques, e.g. p-nitrobenzyloxycarbonyl.

When a penicillin sulfoxide ester of Formula I is reacted with an isocyanate of Formula II in which $n=1$ (i.e. a monoisocyanate), $R^6$ in the resulting penam (III) or cepham (IV) will be the same as $R^5$. If, however, n is greater than 1 (i.e. is 2–4), then the resulting $R^6$ substituent on the penam or cepham may have the structure XII shown above. Thus, if a penicillin sulfoxide ester is reacted with, for example, carbonyl diisocyanate, the initially resulting product will be a carbonyl group which is substituted with two penam moieties, with two cepham moieties, or with one penam moiety and 1 cepham moiety, or a mixture of these products. Such bis-, tris- and tetrakis-penam or cepham compounds may be utilized in that form (after removal of the carboxyl protecting groups) or they may be split to the mono-substituted compounds either under normal workup steps or by subsequent procedures.

After cleavage of the side-chains from the penam (III), cepham (IV) or cephem (V) to produce the free amino compounds of Formula VI, VII or VIII, the latter compounds may be reacylated with a different side-chain to produce compounds of Formula IX, X or XI. Briefly, a compound of Formula VI, VII or VIII is reacted with an acid of the formula

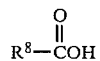
XIII or with an acylating derivative of said acid, in which

is a conventional acyl group known in the penicillin or cephalosporin art. Such conventional acyl groups include, but are not limited to, those exemplified above for $R^2$.

In the acylation of a compound of Formula VI, VII or VIII, the carboxylic acid of formula XIII may be used per se in which case it is preferred to use an enzyme or a condensing agent. Suitable condensing agents include, N,N-dimethylchloroformiminium chloride, an N,N'-carbonyldiimidazole or an N,N'-carbonyldi-triazole, a carbodiimide reagent [especially N,N'-dicyclohexylcarbodiimide, N,N'-diisopropylcarbodiimide or N-cyclohexyl-N'-(2-morpholinoethyl)carbodiimide], an alkynylamine reagent, isoxazolium salt reagent, ketenimine reagent, hexachlorocyclotriphosphatriazine or hexabromocyclotriphosphatriazine, diphenylphosphoryl azide (DPPA), diethylphosphophorylcyanide (DEPC), diphenylphosphite or N-ethoxycarbonyl-2-ethoxy-1,2-dihydroquinoline (EEDQ).

As an alternative to using the carboxylic acid XIII in the above process, there may also be employed reactive acylating derivatives of acid XIII, i.e. functional equivalents of the acid as acylating agents for a primary amino group. Examples of reactive acylating derivatives of the carboxylic acid include the acid halide (e.g. acid chloride or acid bromide), acid anhydrides, including mixed anhydrides (e.g. alkoxyformic anhydrides), acid azides, active esters (e.g. p-nitrophenyl) and active thioesters. Another reactive derivative of the acid is a corresponding azolide, i.e. an amide of the acid whose amide nitrogen is a member of a quasiaromatic five-membered ring containing at least two nitrogen atoms, i.e. imidazole, pyrazole, the triazoles, benzimidazole, benzotriazole and their substituted derivatives. The general method for preparation of azolides is described, for example, in U.S. Pat. No. 3,910,900.

Mention was made above of the use of enzymes to couple the free acid with a compound of Formula VI, VII or VIII. Included in the scope of such processes are the use of an ester, e.g. the methyl ester, of that free acid with enzymes provided by various microorganisms, e.g. those described in *J. Am. Chem. Soc.*, 94(11), 4035–4037 (1972), *J. Antibiotics* (Japan), 24(5), 321–323 (1971) and U.S. Pat. No. 3,682,777.

The acylation process is conducted in a reaction-inert solvent system which can be aqueous or non-aqueous. Suitable reaction-inert solvents include, for example, water, acetone, tetrahydrofuran, dioxane, acetonitrile, dimethylformamide, dimethylsulfoxide, methylene chloride, chloroform, benzene, toluene, methyl isobutyl ketone and mixtures of the above-mentioned organic solvents with water. The choice of solvent, i.e. particularly whether an aqueous or non-aqueous solvent is used, is dependent on the particular starting materials employed. Thus, for example, if the starting compound of Formula VI, VII or VIII is used in the form where the 3- or 4-carboxyl moiety is protected by an ester group cleaved by hydroxylic solvents, e.g. a silyl or stannyl ester, an aprotic organic solvent is most preferably employed. When the starting compound of Formula VI, VII or VIII is used in its salt form, water or an aqueous organic solvent system is preferably employed. The most advantageous solvent system for the particular reagents used can be determined by routine experimentation.

The duration and temperature of the acylation reaction are not critical. Temperatures in the range of from about $-30°$ C. to about $+50°$ C. are commonly used for reaction times ranging from less than one hour up to a day or more. Although the initial contacting of the reactants is preferably carried out at around 0° C. to reduce the incident of by-products, it is frequently desirable after a few minutes of mixing to allow the reaction mixture to warm to room temperature until the reaction is complete.

Any of compounds III–XI of this invention, after removal of the carboxyl-protecting group $R^7$, may be converted, if desired, to a pharmaceutically acceptable salt or to a physiologically hydrolyzed ester such as the pivaloyloxymethyl, acetoxymethyl, phthalidyl, 5-indanyl or methoxymethyl ester.

As shown by the wavy lines in the structural formula for Compound I, the substituents on the 6-position may have either stereochemical configuration, i.e. the amino moiety may have the normal β configuration and $R^3$ the normal α configuration, or these may be reversed. Whatever the configuration at the 6-position of starting Compound I, the same configuration will be maintained in the penam, cepham or cephem product.

However, the configuration of the 2-position of penam III or the 3-position of cepham IV is dependent on the configuration of the sulfoxide moiety of starting Compound I. Thus, as shown in the following equations, the S sulfoxide (Ia) gives primarily the R penam (IIIa) or S cepham (IVa), while the R sulfoxide (Ib) gives primarily the S penam (IIIb) or the R cepham (IVb), which readily eliminates to the cephem.

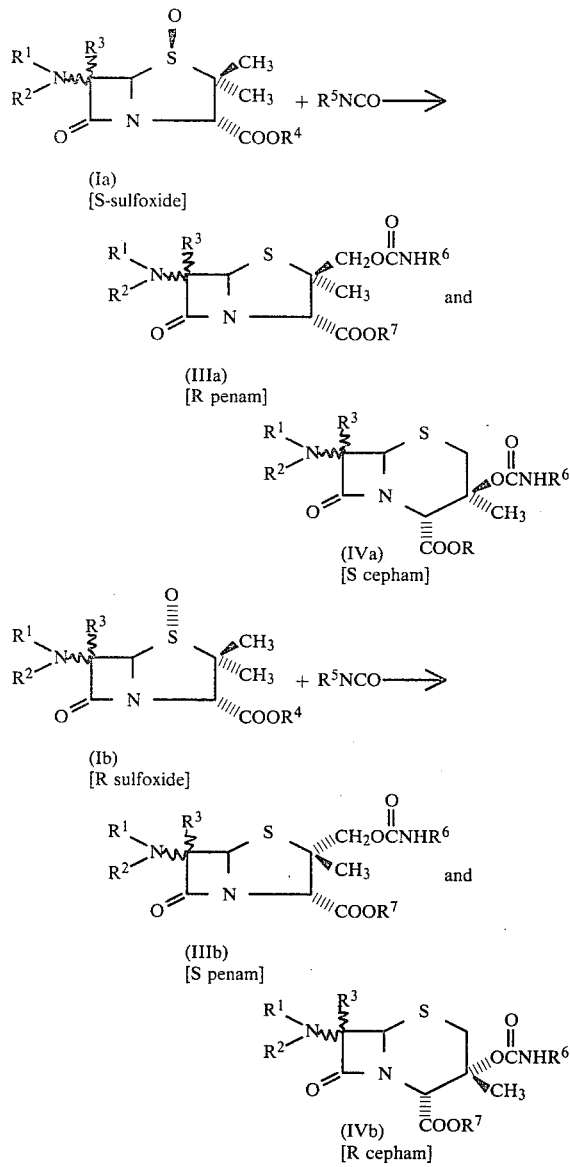

Depending on the particular substituent groups on the starting penicillin sulfoxide, small to moderate amounts of the product having the alternate configuration may also be produced.

The reaction of penicillin sulfoxides of Formula I with isocyanates of Formula II to produce the penams of Formula III and/or the ring-expanded cephams and cephems of Formulae IV and V, respectively, is completely unprecedented. The literature indicates that sulfoxides react with activated isocyanates such as acyl isocyanates to produce sulfilimines. The literature also indicates that activated isocyanates such as acyl isocyanates react with amides to give acyl ureas and amidines (see, for example, H. Ulrich, Chemical Reviews, 65, 369 (1965)). It would therefore be expected that penicillin sulfoxides would give such unwanted products upon reaction with activated isocyanates such as those described herein, particularly at elevated temperatures. To our surprise, we have found that acyl isocyanates and other activated isocyanates of Formula II, above, react with penicillin sulfoxides (in which the carboxyl group is blocked) to give the new 2-carbamoyloxymethylpenams of Formula III and 3-carbamoyloxycephams of Formula IV, as well as the corresponding 3-methyl-$\Delta^3$-cephems of Formula V.

In terms of the ring-expansion aspect of the present invention, the use of isocyanates of Formula II offer several advantages over presently known ring expansion processes, e.g.

(1) Isocyanates of Formula II maintain an anhydrous situation throughout the ring expansion reaction, thus avoiding the water-induced degradation reactions which can occur in catalytic ring expansion processes.

(2) Ring expansion utilizing isocyanates of Formula II are faster than catalytic ring expansion processes.

(3) Isocyanates of Formula II are twice as effective in scavenging active hydrogen compounds than the trimethylsilyl compounds used in some other processes. Thus, one molecule of water is scavenged by one isocyanate group or by two trimethylsilyl groups.

(4) Isocyanates such as acetyl isocyanate, methanesulfonyl isocyanate, sulfonyl diisocyanate, carbonyl diisocyanate and phosphorous triisocyanate give, as reaction by-proucts, acetamide+$CO_2$, methanesulfonamide+$CO_2$, sulfonamide+$CO_2$, urea+$CO_2$ and phosphorous amides+$CO_2$, respectively. These are simpler to handle and dispose of than by-products from processes utilizing bistrimethylsilyl urea, i.e. urea+hexamethyldisiloxane. Further, such neutral amide by-products do no react with the lactam ring.

(5) Many of the isocyanates of Formula II are substantially less expensive than bistrimethylsilyl urea and other trimethylsilyl ureas utilized in other ring expansion processes.

(6) Many of the isocyanates of Formula II are liquids at room temperature. From a practical plant point of view, liquids are easier, and generally safer and less costly to dispense and handle than solids. Most of the silyl compounds utilized in other ring-expansion processes are solids.

(7) From a practical point of view, isocyanates of Formula II may be selected such that their by-products are easily separated from the desired product by different techniques. For example, acyl isocyanates give water-soluble amides as by-products. Silicon tetraisocyanate, on the other hand, gives silica as a by-product, which is completely insoluble in either organic or aqueous solvents.

The starting compounds for use in the present process are either known (many are commercially available) or may be prepared by known procedures from readily available materials. Many of the penicillin sulfoxides of Formula I are known; others may be prepared from the corresponding penicillin by standard techniques well known to those skilled in the art, e.g. by use of sodium metaperiodate, hydrogen peroxide in acetic acid, m-chloroperbenzoic acid, iodobenzene dichloride in aqueous pyridine, ozone, or aqueous bromine. The penicillins themselves also are either known or may be prepared by acylating 6-aminopenicillanic acid with the appropriate side-chain acid, using standard procedures known in the art.

The isocyanates of Formula II also are known or are readily prepared by known techniques from available starting materials. Thus, acetyl isocyanate and similar isocyanates may be prepared by the procedure described in Berichte, 36, 3213 (1903); the preparation of chloroacetyl isocyanate is described in J. Org. Chem., 27, 3742 (1962); the preparation of silicon tetraisocyanate is described in Inorganic Syntheses, 8, 27 (1966); the preparation of sulfonyl diisocyanate is described in W. German Pat. Nos. 940,351 and 1,150,093; and the preparation of methylsulfonyl isocyanate is described in J. Org. Chem., 39, 1597 (1974). General procedures for the preparation of many sulfonyl isocyanates are given in Chemical Reviews, 65, 369 (1965) and references cited therein.

The penams of Formulae III and IX, the cephams of Formulae IV and X, and the cephems of Formulae V and XI provided by the present invention (after removal of the carboxyl-protecting group to produce the free acid) are active against various Gram-positive and Gram-negative organisms and, accordingly, are useful antibacterial agents for the treatment of diseases caused by such organisms in animals, including man.

The free-amino compounds of Formulae VI, VII and VIII obtained by side-chain cleavage of the compounds of Formulae III, IV and V, respectively, generally have lower antibacterial activity than compounds III–IV or IX–XI. Although they may sometimes be utilized therapeutically, their primary utility is as intermediates in the preparation of compounds of Formulae IX–XI by reacylation of the free amino group.

The antibacterial compounds provided by the present invention may be used alone or as the (or an) active ingredient in a conventional pharmaceutical composition, by analogy with other penicillins and cephalosporins. They may be administered orally, parenterally or by suppository. For oral administration the compositions may be in the form of tablets, capsules, powders, granules, lozenges, solutions or suspensions. They may contain conventional excipients suitable to the dosage form, e.g. binding agents, fillers, lubricants, disintegrating agents, wetting agents, stabilizers, sweetening agents, flavors, and the like. Suppositories will contain conventional suppository bases. For parenteral administration, one may utilize fluid unit dosage forms such as sterile solutions or suspensions, or sterile powders intended for reconstitution with a sterile vehicle prior to administration. Conventional adjuvants such as preservatives, buffering agents, suspending agents, and the like may be included in parenteral compositions.

The compositions may contain from 0.1% to 99% by weight of the antibacterial compounds of the present invention. When the compositions are in unit dosage form, each unit will contain from about 100–750 mg of the active ingredient. They are administered in an amount of from about 15 to about 250 mg/kg/day in divided doses, e.g. 3 to 4 times per day.

It will be appreciated by those skilled in the art that the penams (III and IX), cephams (IV and X) and cephems (V and XI) provided by the present invention potentially contain an asymmetric carbon atom in their side-chain. It is specifically intended that this invention include all possible epimers, as well as mixtures thereof.

The Minimum Inhibitory Concentrations (MIC's) of some of the compounds of this invention were determined against a number of organisms, and the results are shown in Table 1. The substituents "R" and "X" in Table 1 refer to the stated substituents on the following skeletal structure

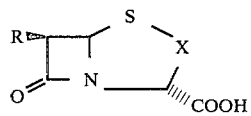

This invention is illustrated by, but in no way limited to, the specific Examples.

TABLE 1

| Compound | Organism Minimum Inhibitory Concentration (μg/ml) | | | | |
|---|---|---|---|---|---|
| | S. pneumoniae A-9585 | S. pyogenes A-9604 | S. aureus A-9537 | S. aureus A-9537 +50% serum | S. aureus A-9606 (pen resist) |
| R = $C_6H_5OCH_2CONH-$<br>X = $>C<^{CH_2OCONHCOCH_3}_{CH_3}$ | 0.06 | — | 0.25 | 2 | >125 |
| R = $C_6H_5OCH_2CONH-$<br>X = $>C<^{CH_2OCONH_2}_{CH_3}$ | 0.016 | 0.008 | 0.06 | 0.06 | >125 |
| R = naphthyl-$OC_2H_5$-CONH−<br>X = $>C<^{CH_2OCONHCOCH_3}_{CH_3}$ | 0.13 | 0.25 | 2 | 8 | 4 |
| R = naphthyl-$OC_2H_5$-CONH−<br>X = $>C<^{CH_2OCONH_2}_{CH_3}$ | 0.03 | 0.06 | >1 | 8 | 4 |

TABLE 1-continued

| Compound | S. pneumoniae A-9585 | S. pyogenes A-9604 | S. aureus A-9537 | S. aureus A-9537 +50% serum | S. aureus A-9606 (pen resist) |
|---|---|---|---|---|---|
| R = 2,6-dichlorophenyl-C(=N-O-)—C(CH₃)=CH—CONH—<br>X = >C(CH₃)(CH₂OCONHCOCH₃) | 0.25 | — | 2 | 32 | 4 |
| R = 2,6-dichlorophenyl-C(=N-O-)—C(CH₃)=CH—CONH—<br>X = >C(CH₃)(CH₂OCONH₂) | 0.5 | 0.5 | 2 | 16 | 4 |
| R = C₆H₅CH(NH₂)CONH—<br>X = >C(CH₃)(CH₂OCONHCOCH₃) | 0.13 | 0.13 | 2 | 2 | >125 |
| R = C₆H₅—C(=N-O-)—C(CH₃)=CH—CONH—<br>X = >C(CH₃)(CH₂OCONHCOCH₃) | 0.5 | 0.5 | 4 | 16 | 4 |
| R = C₆H₅CH₂CONH—<br>X = >C(CH₃)(CH₂OCONHCOCH₃) | 0.06 | — | 0.5 | 1 | >125 |
| R = C₆H₅OCH₂CONH—<br>X = >CH₂ \| >C(CH₃)(OCONHCOCH₃) | 4 | — | >8 | >63 | 125 |
| R = H₂N—<br>X = >C(CH₃)(CH₂OCONHCOCH₃) | 31 > 16 | 32 | >125 | >63 | >125 |
| R = H₂N—<br>X = >C(CH₃)(CH₂OCONH₂) | 1 | 4 | >125 | >63 | >125 |

EXAMPLE 1

(A) (2R,3S,5R,6R) 2-(N-Acetyl)carbamoyloxymethyl-2-methyl-6-phenoxyacetamidopenam-3-carboxylic Acid p-Nitrobenzyl Ester A solution of (1S,3S,5R,6R) 2,2-dimethyl-6-phenoxyacetamidopenam-3-carboxylic acid-1-oxide p-nitrobenzyl ester (25.18 g, 50.0 mmol), acetyl isocyanate (8.50 ml, 9.53 g, 112 mmol), and dioxane (250 ml) was refluxed under nitrogen for 5 hours, cooled and concentrated in vacuo to a yellow foam. The foam was chromatographed on silica gel (1.7 Kg) with methylene chloride: acetone; 9:1; v:v to give four products; the 3-methyl-Δ³-cephem; starting sulfoxide, the title penam, and the cepham (in order of elution). The penam fractions were concentrated to a colorless foam in 40.2% yield (11.80 g). Re-chromatography of a portion gave an analytical sample: m.p. 83°–85°; nmr 100 MHz (CDCl₃) ppm 8.40

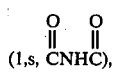

8.20 (2, d, J=8.5, ½ aromatic AB pNB), 7.56 (3, d, J=8.5 over m, ½ AB, pNB and C₆—NH), 7.5 (2, m) and 6.9 (3, m, O—Ph—H's), 5.7 (2, m's, C₅—C₆—H's), 5.32 (2, br s, pNB methylene), 4.88 (1, s, C₃—H), 4.56

(2, s, OCH$_2$C), 4.26 and 4.06 (2, d's, J=11.5, AB of C$_2$—C$\underline{H}_2$O), 2.22

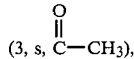
(3, s, C—CH$_3$), and 1.47 (3, s, C$_2$—CH$_3$); nmr $^{13}$C 4 carbonyls ca 170 ppm, carbamate carbonyl C 157.0, C$_2$ singlet at 67.4, while C$_2$—$\underline{C}$H$_2$O is t at 72.3, and C$_2$—$\underline{C}$H$_3$ is q at 21.7.

Anal. Calc'd for C$_{26}$H$_{26}$N$_4$O$_{10}$S: C, 53.23; H, 4.47; N, 9.55. Found: C, 53.21; H, 4.49; N, 9.39.

(B) (3S,4R,5R,6R) 3-(N-acetyl)carbamoyloxy-3-methyl-7-phenoxyacetamidocepham-4-carboxylic acid p-nitrobenzyl ester The final chromatographic band from Step A, above, was concentrated in vacuo to give the title cepham in 12.4% yield (3.66 g): nmr (CDCl$_3$) 100 MHz ppm 9.89

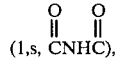
(1,s, CNHC), 8.23 (2, d, J=8.2 Hz, ½ pNB AB), 7.56 (2, d, J=8.2, ½ pNB AB) 7.24 (2, m) and 6.9 (3, m, OPh—H's), 5.55 (1, dd, J=9.5, 4.0, C$_7$—H), 5.32 (3, br s over m, pNB—C$\underline{H}_2$ and C$_6$—H), 4.94 (1, s, C$_4$—H), 4.52

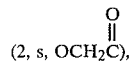
(2, s, OCH$_2$C), 3.56 and 3.34 (2, 2 d's, J=15.5, C$_2$—H$_2$ AB), 2.27

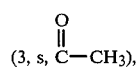
(3, s, C—CH$_3$), and 1.60 (3, s, C$_4$—C$\underline{H}_3$); $^{13}$C 4 carbonyls ca 170 ppm carbamate carbonyl C 157.0, C$_2$ (t, 29.5), C$_3$ (s, 74.3), C$_4$—$\underline{C}$H$_3$ (q, 21.7).

EXAMPLE 2

(2R,3S,5R,6R) 2-(N-Acetyl)carbamoyloxymethyl-2-methyl-6-phenoxyacetamidopenam-3-carboxylic Acid A suspension of 10% palladium on charcoal (400 mg) in ethyl acetate (40 ml) and aqueous 0.5% sodium bicarbonate was prehydrogenated and charged with (2R,3S,5R,6R) 2-(N-acetyl)carbamoyloxymethyl-2-methyl-6-phenoxyacetamidopenam-3-carboxylic acid p-nitrobenzyl ester (400 mg 0.68 mmol). The whole was shaken at 50 psi hydrogen pressure for 30 minutes and polish filtered. The aqueous was washed with ethyl acetate (20 ml), combined with a back extract of H$_2$O (20 ml), overlayed with ethyl acetate (25 ml) and adjusted to pH 2.9 with 35% sulfuric acid. The layers were separated and the rich organic phase was washed with water (20 ml), combined with a back extract (EtOAc, 20 ml), dried (4A sieves), polish filtered and concentrated in vacuo to a colorless foam (270 mg) in 87% yield: nmr 100 MHz (CDCl$_3$—D$_2$O) ppm 7.32 (2, m, m-phenyl H's) 6.96 (3, m, o,p-phenyl H's), 5.59 (2, br s, mag. equiv. C$_5$,C$_6$—H's), 4.79 (1, s, C$_3$—H), 4.59

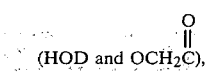
(HOD and OCH$_2$C), 4.08 (m, AB of C$_2$—C$\underline{H}_2$O), 2.25

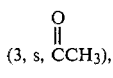
(3, s, CCH$_3$), and 1.58 (3, s, C$_3$—Me) with small ethyl acetate impurity.

EXAMPLE 3

(2R,3S,5R,6R) p-Nitrobenzyl 2-(N-Chloroacetyl)carbamoyloxymethyl-2-methyl-6-(2-phenoxyacetamido)penam-3-carboxylate A solution of (1S,3S,5R,6R) 2,2-dimethyl-6-phenoxyacetamidopenam-3-carboxylic acid-1-oxide p-nitrobenzyl ester (5.01 g, 10.0 mmol) and chloroacetyl isocyanate (5.0 g, 40 mmol) in dioxane (50 ml) was heated at reflux under nitrogen for 4 hours. The solution was concentrated in vacuo and crudely separated by filtration through silica gel (75 g) with methylene chloride:acetone (9:1 v/v). The filtrate was concentrated and chromatographed on silica gel (140 g) with the same solvent. The second of three product bands (cephem, penam, and cepham) was concentrated in vacuo to crude product (0.53 g) a portion of which (0.23 g) was crystallized from hot methanol (5 ml, Darco) to return the title compound as a colorless solid (0.11 g): nmr (CDCl$_3$, 100 MHz) ppm 8.46

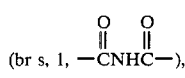
(br s, 1, —CNHC—), 8.21 (d, 2, J=13.2 Hz, ½ aromatic AB p-NO$_2$benzyl), 7.4 (overlapping m's, 5, ½ AB, acyl NH, and orthophenoxy), 6.95 (m's, 3, m,p-phenoxyl), 5.7 (overlapping m's, 2, C$_5$,C$_6$—H's), 5.30 (s, 2, benzyl-C$\underline{H}_2$), 4.81 (s, 1, C$_3$—H), 4.54 (s, 2, phenoxyacetyl C$\underline{H}_2$); 4.25 (overlapping AB m's, 4, ClCH$_2$ and C$_2$—CH$_2$O), and 1.45 (s, 3, CH$_3$); $^{13}$C nmr consistent with four carbonyls ca 170 ppm and carbamate carbonyl at 157.2 ppm.

EXAMPLE 4

(A) (2R,3S,5R,6R) 2-carbamoyloxymethyl-2-methyl-6-(2-ethoxynaphthoylamido)penam-3-carboxylic Acid p-Nitrobenzyl Ester A solution of trichloroacetyl isocyanate (4.2 ml, 6.6 g, 35 mmol), (1S,3S,5R,6R) 2,2-dimethyl-6-(2-ethoxynaphthoylamido)penam-3-carboxylic acid-1-oxide p-nitrobenzyl ester (7.35 g, 12.5 mmol), and dioxane (65 ml) was refluxed under nitrogen for 3.5 hours and concentrated in vacuo to an oil. The oil was taken into methanol (125 ml), the solution was adjusted to pH 7.4 with 5% sodium bicarbonate, and the mixture was held at pH 7.4 to 7.5 with 3% H$_2$SO$_4$ for 2 hours. A precipitate was removed by filtration with a methanol wash (20 ml), and the filtrate was distributed between methylene chloride (250 ml) and water (80 ml). The organic layer was washed with water (75 ml), combined with a back-extract (CHCl₂, 75 ml), dried (4A sieve), polish filtered, and concentrated in vacuo.

The concentrate was chromatographed on silica gel (500 g) with CH₂Cl₂:acetone, 9:1, v:v to give three major products; the Δ³ cephem, the title penam, and the cepham (see below). The middle fractions were concentrated to a very pale yellow foam (1.49 g) 19.6%: nmr 100 MHz (CDCl₃) ppm 8.41 (2, d, J=9 Hz, ½ aromatic AB pNB), 8.0–7.1 (9, aromatics +NH), 6.08 (1, dd, J=4.2, 9, C₆—H), 5.74 (1, d, J=4.2, C₅—H), 5.36 and 5.21 (2, d's, J=13, AB pNB methylene), 4.73 (1, s, C₃—H), 4.60 (2, br s, NH₂), 4.21 (q, J=7) with 4.12 (d, J=11.5, total 3, OCH₂CH₃ and C₂—CHHO—), 3.84 (1, d, J=11.5, C₂—CHHO), and 1.40 (t, J=7) with 1.38 (s, total 6, CH₂CH₃ and C₂—CH₃).

(B) (3S,4R,5R,6R)-3-Carbamoyloxy-3-methyl-7-(2-ethoxynaphthoylamido)cepham-4-carboxylic Acid p-Nitrobenzyl Ester The last major product fractions of Step A, above, were concentrated in vacuo to give the title product as a light yellow foam (2.6%, 0.20 g); nmr CDCl₃ 80 MHz ppm 8.5–6.9 (7, m's, aromatics and C₇—NH), 5.96 (1, dd, J=9.3, 4.5 Hz, C₇—H), 5.44 (1, d, J=4.5, C₆—H), 4.21 (2, s, pNB CH₂), 4.87 (1, s, C₄—H), 4.71 (2, br s, —NH₂), 4.24 (2, q, J=7.0, CH₂—CH₃), 3.54 (1, br d, J=14.6, ½ C₂AB), 3.28 (1, d, J=14.6, ½ C₂AB), and 1.48 (s, C₃—CH₃) with 1.44 (t, J=7.0, total 6).

EXAMPLE 5

(2R,3S,5R,6R) 2-carbamoyloxymethyl-2-methyl-6-(2-ethoxynaphthoylamido)penam-3-carboxylic Acid The p-nitrobenzyl ester of the title compound (610 mg, 1.0 mmol) was added to a prehydrogenated suspension of 10% palladium on carbon in ethyl acetate (25 ml) and aqueous potassium bicarbonate (0.4%, 20 ml). The whole was shaken at 50 psi hydrogen pressure for 60 minutes, and centrifuged. The organic phase and the solids were extracted with 0.2% KHCO₃ (2×20 ml) and the combined aqueous phase was washed with methylene chloride (20 ml). The aqueous phase was stirred with fresh CH₂Cl₂ (25 ml) during pH adjustment to 2.0 with 35% sulfuric acid and the layers were separated. The rich organic phase was washed with pH 2 buffer (15 ml), combined with a back extract (CH₂Cl₂, 25 ml), dried (4A sieves), polish filtered, and concentrated in vacuo to a green-tinted foam (170 mg) 36%: nmr 100 MHz (CDCl₃) ppm 8.1–7.1 (8, 3 m's aromatics+ C₆—NH, exchangeable near 7.9), 5.98 (1, dd, J=4, 8.5 Hz, C₆—H), 5.75 (1, d, J=4, C₅—H), 5.54 (2, br s, exchangeable, NH₂), 4.62 (1, s, C₃—H), 4.23 (q, J=7) and 4.19 (d, J=11.5, 3 total, OCH₂CH₃ and ½ CHHO AB), 3.86 (1, d, J=11.5, ½ CHHO), and 1.57 (s) with 1.44 (t, J=7, total 6, C₂—CH₃ and CH₂—CH₃).

EXAMPLE 6

(2R,3S,5R,6R) 2-Carbamoyloxymethyl-2-methyl-6-(2-phenoxyacetamido)penam-3-carboxylic Acid p-Nitrobenzyl Ester A solution of (1S,3S,5R,6R) 2,2-dimethyl-6-phenoxyacetamidopenam-3-carboxylic acid-1-oxide p-nitrobenzyl ester (7.52 g, 15.0 mmol) and trichloroacetyl isocyanate (5.0 ml, 7.9 g, 42 mmol) in dioxane (75 ml) was refluxed under nitrogen for 3.5 hours and concentrated in vacuo. The concentrate was stirred with methanol (100 ml) and the solution was decanted from a black tar with methanol rinses (2×10 ml). The solution was diluted with water (5 ml), adjusted to pH 7.4 with 5% sodium bicarbonate, and held at pH 7.4–7.5 with 3% H₂SO₄ for 2.5 hours. The mixture was distributed between methylene chloride (100 ml) and water (50 ml). The organic phase was washed with water (50 ml), combined with a CH₂Cl₂ back extract (50 ml), dried (4A molecular sieve), polish filtered with CH₂Cl₂ washes (2×20 ml), and concentrated in vacuo to a light brown oil.

The oil was chromatographed on silica gel (500 g) with methylene chloride:acetone, (9:1; v:v) to give the title product, as the second of two major zones, concentrated in vacuo to a pale yellow foam (2.01 g) 25%; identical by nmr and tlc to the analytical sample prepared by a second chromatography and concentration to a colorless foam: mp 76°d; nmr (CDCl₃) 100 MHz ppm 8.22 (2, d, J=9 Hz, ½aromatic AB pNB), 7.52 overlapping 6.8–7.7 (8, d, J=9, ½pNB, with m's phenoxy H's, NH), 5.75 (dd, J=4, 9 C₆—H) with 5.63 (d, J=4, total 2, C₅—H), 5.37 and 5.22 (2, 2 d's J=13.5, AB pNB methylene), 4.73 (1, s, C₃—H), 4.55

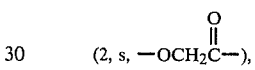

(2, s, —OCH₂C—), 4.16 and 4.00 (2, 2 d's J=11.5, AB C₂—CH₂—O), and 1.41 (3, s C₂—CH₃).

Anal. Calc'd for C₂₄H₂₄N₄O₉S: C, 52.93; H, 4.44; N, 10.29; s, 5.89; Found: C, 52.82; H, 4.51; N, 10.11; s, 5.78.

EXAMPLE 7

(2R,3S,5R,6R) 2-Carbamoyloxymethyl-2-methyl-6-phenoxyacetamidopenam-3-carboxylic Acid The p-nitrobenzyl ester of the title compound (1.09 g 2.0 mmol) was added to a prehydrogenated suspension of 10% palladium on charcoal (0.55 g) in ethyl acetate (50 ml) and 0.4% aqueous potassium bicarbonate (35 ml). The whole was shaken at 50 psi hydrogen pressure for 1.4 hours and filtered, with 0.4% bicarbonate (2×3 ml) and water (5 ml) washes. The layers were separated and the aqueous phase was washed with CHCl₃ (20 ml), combined with an H₂O back extract (10 ml), and stirred with CH₂Cl₂ (25 ml) during pH adjustment to 2.0 with 35% sulfuric acid. The organic phase was separated, washed with pH 2 buffer (10 ml), dried over 4A sieves, polish filtered and concentrated in vacuo to a colorless foam (0.25 g) in 29% yield; nmr 100 MHz (CDCl₃—D₂O) ppm 7.3 (2, m, meta—H's), 7.0 (3 m, o,p—H's), 5.7 (2, m's, C₅,C₆—H's), 4.74 (1, s, C₃—H), 4.59

(2, s, OCH₂C), 4.19 and 4.04 (1 ea, ABq, J=11.5, C₂—CH₂O), 1.58 (3, s, C₂—CH₃).

EXAMPLE 8

(2R,3S,5R,6R) 2-(N-Acetyl)carbamoyloxymethyl-2-methyl-6-[3-(2,6-dichlorophenyl)-5-methylisoxazol-4-ylamido]penam-3-carboxylic Acid p-Nitrobenzyl Ester A suspension of (1S,3S,5R,6R) 2,2-dimethyl-6-[3-(2,6-dichlorophenyl)-5-methylisoxazol-4-ylamido]penam-3-carboxylic acid-1-oxide p-nitrobenzyl ester (6.21 g, 10.0 mmol) in dioxane(50 ml) with acetyl isocyanate (2.3 ml, 30 mmol) was stirred at reflux under nitrogen for 6 hours. The resulting clear solution was concentrated in vacuo to a light orange foam. Chromatography of this foam on silica gel (500 g) with methylene chloride:acetone; 9:1; v:v gave 3 major fractions, the $\Delta^3$ cephem, the title penam, and the cepham analog. The penam was obtained by concentration as an off-white foam in 44% yield (3.12 g): mp 85°d; nmr (CDCl$_3$) 100 MHz ppm 8.23 (d, J=8.5 Hz) overlapping 8.17

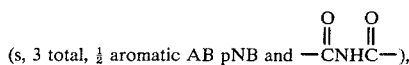

(s, 3 total, ½ aromatic AB pNB and —CNHC—), 7.53 (d, J=8.5) overlapping 7.48 (s, 5 total ½pNB AB and other aromatics), 6.22 (1, d, J=9.5, C$_6$—N$\underline{H}$) 5.79 (1, dd, J=4, 9.5, C$_6$—H), 5.58 (1, d, J=4, C$_5$—H), 5.39 and 5.21 (2, 2 d's, J=13, AB pNB methylene, 4.72 (1, s, C$_3$—H) 4.14 (1, d, J=11, C$_2$—C$\underline{H}$HO), 3.62 (1, d, J=11, C$_2$—CH$\underline{H}$O), 2.81 (3, s, isox—CH$_3$), 2.31

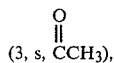

(3, s, $\overset{O}{\overset{\|}{C}}$CH$_3$), and 1.39 (3, s, C$_2$—CH$_3$).

Anal. Calc'd for C$_{29}$H$_{25}$N$_5$O$_{10}$SCl$_2$: C, 49.30; H, 3.57; s, 4.54; Cl, 10.04. Found: C, 49.31; H, 3.83; s, 4.30; Cl, 10.17.

EXAMPLE 9

(2R,3S,5R,6R) 2-(N-Acetyl)-carbamoyloxymethyl-2-methyl-6-phenylacetamidopenam-3 carboxylic Acid p-Nitrobenzyl Ester A solution of (1S,3S,5R,6R) 2,2-dimethyl-6-phenylacetamidopenam-3-carboxylic acid -1-oxide p-nitrobenzyl ester (4.85 g, 10.0 mmol) and acetyl isocyanate (2.3 ml, 30 mmol) in dioxane (50 ml) was refluxed under nitrogen for 7 hours. The light orange solution was concentrated in vacuo to a foam which was chromatographed on silica gel (500 g) with methylene chloride:acetone; 9:1, v:v. Two major bands were eluted; the first was the $\Delta^3$ 3-methylcephem (28%, 1.29 g) and the second was the title compound obtained in 45% yield (2.56 g) as an off-white foam: mp 83°-85°; nmr 100 MHz (CDCl$_3$) ppm 8.24 (2, d, J=9 Hz, ½aromatic AB pNB), 7.61 (2, d, J=9, ½ pNB AB), 7.28 (5, s, phenyl), 5.54 (2, m's C$_6$—C$_5$—H's), 5.40 (2, br s, pNB methylene), 4.91 (1, s, C$_3$—H), 4.27 1, d, J=12, ½ C$_2$—CHHO AB), 4.08 (1, d, J=12, ½C$_2$—methylene AB), 3.12

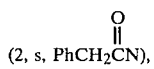

(2, s, PhCH$_2$CN), 2.12 (3, s, acetyl), and 1.41 (3, s, C$_2$—CH$_3$).

Anal. Calc'd. for C$_{26}$H$_{26}$N$_4$O$_9$S: C, 54.73; H, 4.59; N, 9.82. Found: C, 54.53; H, 4.79; N, 9.82.

EXAMPLE 10

(2R,3S,5R,6R) 2-(N-Acetyl)carbamoyloxymethyl-2-methyl-6-(5-methyl-3-phenyl-4-isoxazolyl)amidopenam-3-carboxylic Acid p-Nitrobenzyl Ester A suspension of (1S,3S,5R,6R) 2,2-dimethyl-6-(5-methyl-3-phenyl-4-isoxazolyl)amidopenam-3-carboxylic acid-1-oxide p-nitrobenzyl ester (5.53 g, 10.0 mmol) was treated in refluxing dioxane (50 ml) with acetyl isocyanate (2.3 ml, 30 mmol) for 6 hours. The unreacted ester (1.26 g, 2.3 mmol) was removed by filtration and the filtrate was concentrated in vacuo to a dark yellow foam which was chromatographed on silica gel (500 g) with methylene chloride:acetone, (9:1; v:v). The product fraction was concentrated in vacuo to a colorless foam (1.02 g) in 20.5% yield; nmr 100 MHz (CDCl$_3$) ppm 9.20 (2, d, J=8.5 Hz, ½pNB AB), 8.84

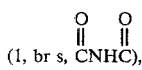

(1, br s, CNHC), 8.50 with 8.46 (7, m's, ½pNB and phenyl H's), 8.23 (1, br d, J=9, C$_6$—N$\underline{H}$), 5.76 (1, dd, J=4, 9, C$_6$—H), 5.51 (1, d, J=4, C$_5$—H), 5.26 and 5.19 (2, ABq, J=13, pNB—CH$_2$), 4.64 (1, s, C$_3$—H), 4.03 (1, d, J=11.5, ½ AB C$_2$—CH$_2$—O), 3.53 (1, d, J=11.5, ½ AB C$_2$—$\underline{H}_2$O), 2.76 (3, s, oxazolyl-Me), 2.27

(3, s, $\overset{O}{\overset{\|}{C}}$CH$_3$)

and 1.33 (3, s, C$_2$—CH$_3$).

EXAMPLE 11

(A) (2R,3S,5R,6R) 2-(N-Acetyl)carbamoyloxymethyl-2-methyl-6-(2-ethoxynaphthoylamido)penam-3-carboxylic Acid p-Nitrobenzyl Ester A mixture of acetyl isocyanate (2.3 ml, 30 mmol), 1S,3S,5R,6R) 2,2-dimethyl-6-(2-ethoxynaphthoylamido)penam-3-carboxylic acid-1-oxide p-nitrobenzyl ester (5.66 g, 10.0 mmol) and dioxane (50 ml) was refluxed for 6 hours and concentrated in vacuo. The concentrate was chromatographed on silica gel (500 g) with methylene chloride:acetone, 9:1, v:v. Four major fractions were obtained; the $\Delta^3$ 3-methyl cepham, the starting sulfoxide, the title penam, and the cepham analog (in order of elution). The "penam" fractions were concentrated in vacuo to a pale yellow foam in 23% yield (1.47 g): mp, 100° d; nmr (CDCl$_3$) 100 MHz ppm 8.29 (2, d, J=9 Hz, ½ aromatic AB pNB), 8.0-7.1 (10, m's, aromatics+NH's), 6.09 (1, dd, J=9, 4, C$_6$—H), 5.77 (1, d, J=4, C$_5$—H), 5.37 and 5.23 (2, 2, d's, J=13 Hz, AB pNB methylene), 4.73 (1, s, C$_3$—H), 4.32 (q, J=7) over 4.29 (d, J=11, 3 total C$\underline{H}_2$CH$_3$ and ½C$_2$—C$\underline{H}$HO), 3.91 (1, J=11, C$_2$—CH$\underline{H}$O), 2.14

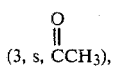

(3, s, $\overset{O}{\overset{\|}{C}}$CH$_3$), and 1.42 (6, s, with t, J=7, C$_2$—CH$_3$ and CH$_2$C$\underline{H}_3$).

Anal. Calc'd for $C_{31}H_{30}N_4O_{10}S$: C, 57.21; H, 4.65; N, 8.61; S, 4.93. Found: C, 57.12; H, 4.72; N, 8.30; S, 4.87.

(B) (3S,4R,5R,6R)-3-(N-Acetyl)carbamoyloxy-3-methyl-7-(2-ethoxynaphthoylamido)cepham-4-carboxylic Acid p-Nitrobenzyl Ester The final product fractions of Step A, above, yielded the title compound as a pale yellow foam in 4.1% (0.27 g) yield; nmr (CDCl$_3$) 100 MHz ppm 8.3–7.1

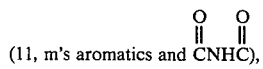
(11, m's aromatics and CNHC), 6.90 (1, br d, J=8.5 Hz, $C_7$—N$\underline{H}$), 6.14 (1, dd, J=4.5, 8.5, $C_7$—H), 5.35 (2, s, pNB C$\underline{H}_2$), 5.16 (1, d, J=4.5, $C_6$—H), 4.26 (2, q, J=7, OC$\underline{H}_2$CH$_3$), 3.60 (1, br d, J=18, ½AB $C_2$—CH$_2$), 3.22 (1, d, J=18, ½AB), 2.18

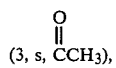
(3, s, CCH$_3$), and 1.58 (br s) with 1.49 (t, J=7, total 6 protons, $C_3$—CH$_3$ and CH$_2$C$\underline{H}_3$).

EXAMPLE 12

(2R,3S,5R,6R) 2-Carbamoyloxymethyl-2-methyl-6-[3-(2,6-dichlorophenyl)-5-methyl-4-isoxazolyl]amidopenam-3-carboxylic Acid p-Nitrobenzyl Ester A mixture of (1S,3S,5R,6R) 2,2-dimethyl-6-[3-(2,6-dichlorophenyl)-5-methyl-4-isoxazolyl]amidopenam-3-carboxylic acid-1-oxide p-nitrobenzyl ester (6.21 g, 10.0 mmol) and trichloroacetyl isocyanate (3.3 ml, 32 mmol) in dioxane (50 ml) was refluxed for 3.5 hours under nitrogen. The light yellow solution was cooled, and concentrated to an oil which was stirred with methanol (100 ml). The methanol solution was decanted, with a methanol wash (2×10 ml), from a little residual oil, and was adjusted to pH 7.4 with 5% sodium bicarbonate. The pH was held at 7.4 to 7.5 with 3% sulfuric acid for 2 hours and the reaction was quenched in methylene chloride (200 ml) and water (100 ml). The rich organic layer was washed with water (100 ml), combined with a back extract (CH$_2$Cl$_2$, 50 ml), dried (4A sieves), polish filtered, and concentrated in vacuo to a yellow oil.

Chromatography of the oil on silica gel (500 g) with methylene chloride:acetone, (9:1; v:v) gave four zones. Following the void volume, fractions of 25 ml were collected; tubes 6–16 containing the $\Delta^3$ 3-methylcephem, tubes 10–18 small amounts of starting sulfoxide, tubes 20–44 the title penam, and tubes 46–74 the corresponding cepham. Tubes 21–40 of the penam fraction were combined and concentrated in vacuo to a clear light cream foam; 29.7% yield (1.97 g): nmr 100 MHz (CDCl$_3$) ppm 8.13 (2, d, J=8.5 Hz, ½aromatic AB pNB), 7.53 (d, J=8.5) with 7.47 (tight m, total 5, ½aromatic AB and dichlorophenyl H's), 6.37 (1, d, J=9.2, $C_6$—NH), 5.80 (1, dd, J=4.0, 9.2, $C_6$—H), 5.55 (1, d, J=4.0, $C_5$—H), 5.37 and 5.20 (2, d's, J=12.8, pNB methylene AB), 5.0 (2, br s, NH$_2$), 4.68 (1, s, $C_3$—H), 4.10 (1, d, J=11.5, ½AB $C_2$—C$\underline{H}_2$O), 3.56 (1, d, J=11.5, ½AB $C_2$—CH$_2$), 2.81 (3, s, isoxazolyl CH$_3$), 1.37 (3, s, $C_2$—CH$_3$).

EXAMPLE 13

(2R,3S,5R,6R) 6-(4-Nitrobenzyloxycarbonyl)amino-2-carbamoyloxymethyl-2-methylpenam-3-carboxylic Acid p-Nitrobenzyl Ester A mixture of (1S,3S,5R,6R) 6-(4-nitrobenzyloxycarbonyl)amino-2,2-dimethylpenam-3-carboxylic acid-1-oxide p-nitrobenzyl ester (8.19 g, 15.0 mmol), trichloroacetyl isocyanate (5.0 ml, 7.9 g, 42 mmol) and dioxane (75 ml) was refluxed under nitrogen for 3.5 hours and concentrated in vacuo to a light brown oil. The oil was stirred with warm methanol (150 ml) for 0.5 hour and the solution was decanted from a small amount of dark residue. The methanol solution was adjusted to pH 7.4 with 5% sodium bicarbonate and held at pH 7.4–7.5 with 3% sulfuric acid during a 2.0 hour stirring period. The mixture was then distributed between methylene chloride (250 ml) and water (100 ml). The organic layer was washed with water (100 ml), combined with a CH$_2$Cl$_2$ back-extract (100 ml), dried (4A molecular sieve), polish filtered, and concentrated in vacuo to a light brown oil.

The oil was chromatographed on silica gel (500 g) with methylene chloride:acetone (9:1 v:v) to give three major bands; (in elution order) the $\Delta^3$3-methylcephem, the title penam and the corresponding cepham. The penam fraction was concentrated in vacuo to a pale yellow foam in 19.7% (1.74 g) overall yield; nmr 100 MHz (CDCl$_3$) 8.23 (d, J=9.5 Hz) with 8.18 (d, J=8.5, total 4, ½ (2) aromatic AB's), 7.55 (d, J=9.5) and 7.50 (d, J=8.5, total 4, other ½(2) aromatic AB's), 6.36 (1, d, J=9.5, $C_6$—NH), 5.63 (1, d, J=4, $C_5$—H), 5.48 (~1, dd, J=4, 9.5, $C_6$—H), 5.31 (m) and 5.24 (s, ~4, pNB methylenes), 5.10 (~2, br s, NH$_2$), 4.73 (1, s, $C_3$—H), 4.25 (1, d, J=12, ½$C_2$ methylene AB), 3.94 (1, d, J=12, other ½ $C_2$CH$_2$O AB), and 1.44 (3, s, CH$_3$). Recrystallization of a portion from ether-methylene chloride returned small colorless needles: mp 80°–81°.

Anal. Calc'd for $C_{24}H_{23}N_5O_{11}S$: C, 48.89; H, 3.93; N, 11.88. Found: C, 48.82; H, 3.97; N, 11.86.

EXAMPLE 14

(2R,3S,5R,6R) 6-Amino-2-carbamoyloxymethyl-2-methylpenam-3-carboxylic Acid

A suspension of 10% palladium on charcoal (0.50 g) in ethyl acetate (25 ml) and aqueous potassium bicarbonate (0.4%, 22.5 ml, 0.10 g inorganics) was prehydrogenated at 50 psi hydrogen for 15 minutes. The suspension was charged under nitrogen with (2R,3S,5R,6R) 6-(4-nitrobenzyloxycarbonyl)amino-2-carbamoyloxymethyl-2-methylpenam-3-carboxylic acid p-nitrobenzyl ester (0.54 g, 0.9 mmol) and the whole was shaken at 50 psi hydrogen pressure for 1.2 hours. The mixture (pH 5.0) was centrifuged and the aqueous phase was washed with methylene chloride (2×15 ml), combined with a water back extract (10 ml), and concentrated to about a 2 ml volume. The rich aqueous phase was diluted with deuterium oxide (4 ml) frozen on dry-ice and lyophilized to give a light yellow solid (0.25 g; theory=0.25 g+inorganics 0.10 g) in 66% product yield; nmr 100 MHz (D$_2$O) ppm 4.63 (1, d, J=4.0 Hz, $C_6$—H), 4.46 (1, s, $C_3$—H), $C_5$—H under HOD, 4.18 (1, d, J=11.5, ½AB $C_2$—C$\underline{H}$H—O), 4.01 (1, d, J=11.5, $C_2$—CH$\underline{H}$O), and 1.53 (3, s, $C_2$—CH$_3$).

EXAMPLE 15

(3S,4R,6R,7R)
7-(4-Nitrobenzyloxycarbonyl)amino-3-carbamoyloxy-3-methylcepham-4-carboxylic Acid p-Nitrobenzyl Ester The title compound was eluted as the final fractions in the chromatographic separation of Example 13 in a yield of 1.1% (0.10 g). The product was equal in nmr and tlc characteristics to an analytical sample prepared in a larger run: mp 79°–80°; nmr 100 MHz (CDCl$_3$) ppm 8.23 (d, J=9.0 Hz) with 8.17 (d, J=8.5, total 4, ½ aromatic AB's p-NO$_2$benzyl), 7.55 (d, J=8.5) with 7.50 (d, J=9.0, total 4, ½ aromatic AB's), 6.47 (1, d, J=9.5, C$_7$—N$\underline{H}$), 5.31 (s) and 5.22 (s) over 5.5–5.2 (m's, total 8, benzyl CH$_2$'s over C$_6$—H, C$_7$—H and NH$_2$), 4.89 (1, s, C$_4$—H), 3.54 (1, br d, J=14.5, ½AB C$_2$$\underline{H}$H), 3.29 (1, d, J=14.5, C$_2$H$\underline{H}$), and 1.53 (3, s, C$_3$—CH$_3$).

Anal. Calc'd for C$_{24}$H$_{23}$N$_5$O$_{11}$S·½H$_2$O: C, 48.15; H, 4.04; N, 11.70; S, 5.36. Found: C, 48.24; H, 3.96; N, 11.68; S, 5.20.

EXAMPLE 16

(6R,7R)
3-Methyl-7-phenoxyacetamidoceph-3-em-4-carboxylic Acid Diphenylmethyl Ester A solution of (1S,3S,5R,6R) 2,2-dimethyl-6-phenoxyacetamidopenam-3-carboxylic acid-1-oxide diphenylmethyl ester monohydrate (5.51 g, 10.0 mmol) in dioxane (50 ml) was stirred over Linde 4A molecular sieves (2 g) for 16 hours and filtered with a dioxane wash (2×15 ml). To the dried solution was added p-toluenesulfonyl isocyanate (4.3 g, 22 mmol), and the mixture was heated at reflux for 7 hours under nitrogen and then concentrated in vacuo to a light orange oil. The residue was distributed between methylene chloride (50 ml) and water-ice (50 ml) with pH adjustment to 8.4 using dropwise addition of 50% NaOH, and back washes with CH$_2$Cl$_2$ (20 ml) and pH 10 phosphate buffer (20 ml). The combined organic extracts were dried (sieves), polish filtered, and concentrated in vacuo to a light yellow foam. The foam was taken into boiling isopropanol (75 ml) and after cooling yielded a glassy solid (6.23 g). A major portion of the solid (5.95 g) was filtered through silica gel (25 g) with CH$_2$Cl$_2$:acetone, 9:1, v/v (120 ml) and the filtrate was concentrated in vacuo to a pale yellow solid (4.02 g, 78%). Crystallization of a portion (2.72 g) from isopropanol (40 ml) returned an off-white microcrystalline solid which was collected, washed with 0° isopropanol (25 ml) and dried in vacuo to give the title compound (1.93 g, 71% recovery, 55% overall). NMR indicated 82% purity, with impurities of p-toluenesulfonamide and isopropanol.

EXAMPLE 17

(6R,7R)
3-Methyl-7-phenoxyacetamidoceph-3-em-4-carboxylic Acid Diphenylmethyl Ester A solution of (1S,3S,5R,6R) 2,2-dimethyl-6-phenoxyacetamidopenam-3-carboxylic acid-1-oxide diphenylmethyl ester monohydrate in dioxane was dried over Linde 4A molecular sieves and an aliquot (18 ml, containing 4.1 mmol of the ester) was charged with pyridine (0.081 ml, 1.0 mmol), acetyl bromide (0.073 ml, 1.0 mmol), and acetyl isocyanate (1.1 ml, 12 mmol). The solution was heated at reflux under nitrogen for 4 hours and concentrated in vacuo to a brown glass which was filtered through silica gel (12 g) with 9:1, v/v methylene chloride:acetone (75 ml) to remove color and impurities. The filtrate was concentrated in vacuo to a yellow foam (1.85 g, 88%). A portion of this solid (1.61 g) was crystallized from hot isopropanol (20 ml) to return the title compound as a yellow solid (1.51 g, 94% recovery, 83% overall) of 90+% purity by n.m.r.

EXAMPLE 18

(2R,3S,5R,6R)
6-Amino-2-carbamoyloxymethyl-2-methylpenam-3-carboxylic Acid p-Nitrobenzyl Ester A solution of (2R,3S,5R,6R) 2-(N-acetyl)carbamoyloxymethyl-2-methyl-6-phenoxyacetamidopenam-3-carboxylic acid p-nitrobenzyl ester (1.17 g, 2.0 mmol) in methylene chloride (10 ml) at −40° was charged with dimethylaniline (1.03 ml, 8.0 mmol) and phosphorous pentachloride (0.92 g, 4.4 mmol). The solution was stirred at −35° to −40° for 30 minutes and cold (~−35°) methanol (4.1 ml, 100 mmol) was added dropwise. The pale green solution was stirred at −35° to −40° for 2 hours and then quenched into ice-water (10 ml). The pH was adjusted to 1.7 with conc. ammonia and the layers were separated. The aqueous was washed with CH$_2$Cl$_2$ (5 ml), combined with a water back-extract (5 ml), and stirred with CH$_2$Cl$_2$ (10 ml) during pH adjustment to 6.5 with ammonia. The organic phase was withdrawn, washed (5 ml, H$_2$O), combined with a back-extract (CH$_2$Cl$_2$, 10 ml), dried (4A sieves), filtered, concentrated to 4 ml and diluted with heptane (10 ml). The suspension was concentrated to 8 ml and the liquids were decanted. The solids were treated with CH$_2$Cl$_2$ (4 ml) and heptane (10 ml) in the same fashion, and the product was washed with heptane and dried to an off-white solid (0.28 g) 34%; nmr 100 MHz CDCl$_3$—D$_2$O δ8.24 (2, d, J=8.5 Hz, ½ pNB AB), 7.56 (2, d, J=8.5, pNB, AB), 5.68 (1, brd J=4, C$_5$—H) 5.32 (2, s, benzyl C$\underline{H}$$_2$), 4.76 (1, s, C$_3$—H) 4.55 (HOD overlapping C$_6$—Hd), 4.16 and 3.97 (2, ABq J=11.5 C$_2$—C$\underline{H}$$_2$—O), 1.43 (3, s, C$_3$—C$\underline{H}$$_3$), with 2.36 (¾, s,

of impurity N-acetyl analog; ~25 mol %).

EXAMPLE 19

(6R,7R)
3-Methyl-7-phenoxyacetamidoceph-3-em-4-carboxylic Acid Diphenylmetyl Ester (1S,3S,5R,6R) 2,2-Dimethyl-6-phenoxyacetamidopenam-3-carboxylic acid-1-oxide diphenylmethyl ester (25.00 gms, 45.41 mmoles) was dissolved in sieve-dried, peroxide-free dioxane (250 mls) at 25° C. with good agitation. To this solution, in order, were added pyridine (10.99 mls, 10.78 gms, 136.22 mmoles), acetyl bromide (0.67 mls, 1.12 gms, 9.08 mmoles) and dimethylsilyl diisocyanate (16.14 gms, 113.51 mmoles), and the slurry was heated to reflux (ca. 100° C.) for 4 hours. The dioxane slurry was then cooled to 25° C., filtered, and concentrated in vacuo at 50° C. to a heavy oil. The oil was taken up in methylene chloride (400 mls), stirred for 15 minutes at 25° C., filtered, and concentrated in vacuo to dryness. The residue was dissolved in hot 1-butanol (500 mls, ca. 90°–95° C.) and allowed to cool to 25° C. The slurry was cooled to 0°–5° C. for 16 hours, filtered, washed with cold butanol (0°–5° C., 100 mls), then with Skellysolve B (200 mls), and oven-dried at 45° C. to constant weight. Yield: 20.2 gms, 86.4% of snow-white crystalline title compound. The NMR spectrum was clean and consistent for the desired structure, as follows: 80 MHz H' NMR, $\delta(CD_2Cl_2)$ 2.08 (3H, s, $CH_3$), 3.04–3.62 (2H, m, $CH_2$, $J_{AB}=18.1$ Hz), 4.55 (2H, s, $CH_2$), 4.99–5.05 (1H, d, β-lactam H, $J_A=4.7$ Hz), 5.74–5.91 (1H, m, β-lactam H, J=4.7 Hz), 6.75–7.50 (17H, m, aromatic CH, and NH).

EXAMPLE 20

(6R,7R) 3-Methyl-7-phenoxyacetamidoceph-3-em-4-carboxylic Acid Diphenylmethyl Ester (1S,3S,5R,6R) 2,2-Dimethyl-6-phenoxyacetamidopenam-3-carboxylic acid-1-oxide diphenylmethyl ester (55.06 gms, 100.00 mmoles) was dissolved in sieve-dried, peroxide-free dioxane (550 mls) at 25° C. with good agitation. To this solution, in order, were added pyridine (24.21 mls, 23.73 gms, 300.00 mmoles), acetyl bromide (1.48 mls, 2.46 gms, 20.00 mmoles) and methylsilyl triisocyanate (89% pure, 21.30 mls, 25.34 gms, 133.33 mmoles). The slurry was heated to reflux (ca 100° C.) for 4 hours. The reaction mixture was then cooled to 25° C. and filtered, with the clear yellow filtrate being concentrated in vacuo at 50° C. to a highly viscous oil. The oil was dissolved in hot 2-propanol (~80° C., 3000 mls), filtered, and allowed to cool to 25° C. The slurry was cooled to 0°–5° C. for 2 hours, filtered, and washed with 2-propanol (0°–5° C., 400 mls), and oven-dried at 45° C. to constant weight. Yield: 38.6 gms, 75% of white crystalline title compound. The 80 MHz H' NMR spectrum was clean and consistent for the desired structure.

EXAMPLE 21

(2R,3S,5R,6R) 2-(N-Acetyl)carbamoyloxymethyl-6-amino-2-methylpenam-3-carboxylic Acid p-Nitrobenzyl Ester A solution of (2R,3S,5R,6R) 2-(N-acetyl)carbamoyloxymethyl-2-methyl-6-phenoxyacetamidopenam-3-carboxylic acid p-nitrobenzyl ester (4.68 gm, 8 mmols) in dry methylene chloride (40 ml) was cooled to −60° under nitrogen. It was charged with dimethylaniline (4.06 gm, 33.5 mmol) and phosphorus pentachloride (3.68 gm, 17.7 mmol) and stirred for 30 minutes at −64° to −56°, during which time the phosphorus pentachloride dissolved. A solution of dry methanol (8.10 ml) in dry methylene chloride (8.10 ml) was then slowly added at −55° to −45°. The reaction mixture was stirred for 20 minutes at −60° to −55° and then poured into 16 ml of ice-water. The pH was adjusted to 1.7 with concentrated ammonia and the layers were separated. The methylene chloride layer was washed with 20 ml of pH 2.0 buffer which was separated and combined with the aqueous layer. Methylene chloride (20 ml) was added to the combined aqueous layers and the mixture was adjusted to pH 6.5 with concentrated ammonia. The phases were separated, the water was washed with 20 ml of methylene chloride, and the combined methylene chloride layers were dried over molecular sieves. After filtration, the solution was concentrated in vacuo to about 20 ml and then added dropwise to 400 ml of stirring heptane. The heptane was decanted from the solid which precipitated and was replaced by 100 ml of fresh heptane. The suspension was thoroughly stirred, filtered, washed, air dried, and finally dried in vacuo. There was obtained 1.66 gm of the title product as a white amorphous solid. The purity was estimated from its nmr spectrum to be about 90%, the remainder being primarily the non-acetylated material.

EXAMPLE 22

(2R,3S,5R,6R) 2-(N-Acetyl)carbamoyloxymethyl-6-amino-2-methylpenam-3-carboxylic Acid To a prehydrogenated suspension of 10% palladium on carbon (0.83 gm), water-washed ethyl acetate (8.3 ml) and water (4.1 ml) was added (2R,3S,5R,6R) 2-(N-acetyl)carbamoyloxymethyl-6-amino-2-methylpenam-3-carboxylic acid p-nitrobenzyl ester (0.83 gm, 1.84 mmol). The mixture was shaken at 50 psi hydrogen pressure for 80 minutes and filtered through Dicalite-coated paper. The aqueous phase was separated, concentrated at reduced pressure to remove volatile solvent and gases, frozen and lyophilized. There was obtained 0.38 gm of the title compound as a white amorphous solid. Its nmr spectrum was consistent with the desired product.

EXAMPLE 23

(2R,3S,5R,6R) 2-(N-Acetyl)carbamoyloxymethyl-6-[(R)-2-Amino-2-phenylacetamido]-2-methylpenam-3-carboxylic Acid p-Nitrobenzyl Ester A solution of (2R,3S,5R,6R) 2-(N-acetyl)carbamoyloxymethyl-6-amino-2-methylpenam-3-carboxylic acid p-nitrobenzyl ester (0.80 gm, 1.77 mmol) in methylene chloride (10 ml) was cooled to 2° and dimethylaniline (0.214 gm, 1.77 mmol) was added. To the stirred mixture was added (−)-phenylglycyl chloride hydrochloride (0.392 gm, 1.83 mmol) in two equal portions. The first portion was added at 2° and the reaction mixture was gradually warmed to 20° over a 90 minute period. The reaction did not appear to begin at the lower temperatures. The second portion of the acid chloride was added at 20° and the reaction mixture was stirred at room temperature for 4½ hours. Water (10 ml) was added and, with thorough mixing, the pH was adjusted to 1.7. The layers were separated, the water layer was washed with methylene chloride, and the methylene chloride layer was washed with pH 2.0 buffer. The aqueous layers were combined, adjusted to pH 7.0 with 10% KOH solution, and extracted with methylene chloride (2×10 ml). The methylene chloride extracts were combined, dried over molecular sieves and concentrated in vacuo to about 15 ml. This solution was added dropwise to 300 ml of stirring heptane and produced a fine white amorphous solid. This was removed by filtration and dried to give 0.61 gms of the title product. The purity was estimated from its nmr spectrum to be about 60%.

EXAMPLE 24

(2R,3S,5R,6R) 2-(N-Acetyl)carbamoyloxymethyl-6-[(R)-2-amino-2-phenylacetamido]-2-methylpenam-3-carboxylic Acid To a prehydrogenated suspension of 10% palladium on carbon (0.59 gm), water-washed ethyl acetate (6.0 ml) and water (3.0 ml) was added (2R,3S,5R,6R) 2-(N-acetyl)carbamoyloxymethyl-6-[(R)-2-amino-2-phenylacetamido]-2-methylpenam-3-carboxylic acid p-nitrobenzyl ester (0.59 gm. 1.06 mmol). The mixture was shaken at 50 psi hydrogen pressure for 3 hours at 25° and then filtered through Dicalite-coated paper. The aqueous phase was separated, concentrated at reduced pressure to remove volatile solvent and gases, frozen and lyophilized. There was obtained 0.30 gm of the title compound as an amorphous solid. The purity was estimated from its nmr spectrum to be 60–70%.

EXAMPLE 25

Percentage OF Penam, Cepham And Cephem Formed In The Reaction OF [1S,3S,5R,6R] 2,2-Dimethyl-6-phenoxyacetamidopenam-3-carboxylic Acid-1-oxide Diphenylmethyl Ester With Different Isocyanates Under Varying Conditions And With Varying Subsequent Treatment Of The Initial Product A 5% solution of [1S,3S,5R,6R] 2,2-dimethyl-6-phenoxyacetamidopenam-3-carboxylic acid-1-oxide diphenylmethyl ester in dioxane was prepared. Aliquots of the above solution containing 5.51 gms (10 mmols) of the penicillin sulfoxide ester were charged with 30 mmols (300 mole %) of the indicated isocyanate (and, where indicated, with pyridine and/or acetyl bromide). The solutions were refluxed under nitrogen for 4 hours and then concentrated in vacuo to dryness. When indicated, portions of the resulting products were further treated with base or filtered through silica gel with methylene chloride:acetone (9:1, v:v), and concentrated to dryness. The residues were analyzed for approximate percentages of penam, cepham and $\Delta^3$-cephem by integration of the nmr methyl group signals at ca. $\delta 1.2$ for the penams, ca. $\delta 1.5$ for the cephams and ca. $\delta 2.11$ for the $\Delta^3$-cephems.

| Mole % Pyridine | Mole % $CH_3CBr=O$ | % Penam | % Cepham | % Cephem |
|---|---|---|---|---|
| | p-Toluenesulfonyl isocyanate | | | |
| (a) | 0　0 | 57 | 41 | 2 |
| (b) | Product of (a) treated in methylene chloride with tetramethylguanidine; latter then removed with water washes. | 0 | 7 | 93 |
| (c) | Product of (a) filtered through silica gel. | 0 | 92 | 8 |
| | Methanesulfonyl isocyanate | | | |
| (d) | 0　0 | 63 | 27 | 10 |
| (e) | 20　0 | 57 | 9 | 34 |
| (f) | 50　0 | 50 | 0 | 50 |
| (g) | Product of (f) filtered through silica gel. | 15 | 0 | 85 |
| (h) | Product of (d) in methylene chloride washed with pH 8.5 water and held 2 hrs. | 10 | 20 | 70 |
| (i) | Product of (d) treated in methylene chloride with dimethylformamide; latter removed with water washes | 55 | 0 | 45 |
| (j) | Product of (d) filtered through silica gel. | 45 | 30 | 25 |
| | Trichloroacetyl isocyanate | | | |
| (k) | 0　0 | 26 | 56 | 18 |
| | Acetyl isocyanate | | | |
| (l) | 0　0 | 70 | 25 | 5 |
| (m) | 50　0 | 70 | 25 | 5 |
| (n) | 0　20 | 68 | 30 | 2 |
| (o) | 25　25 | 0 | 10 | 80 |
| | Methoxycarbonyl isocyanate | | | |
| (p) | 0　0 | 37 | 38 | 0 |

Note:
Product (o) also contained about 10% of an unidentified impurity appearing at ca. $\delta$ 1.6.
Product (p) also contained about 25% of an unidentified impurity appearing at ca. $\delta$ 1.9.

EXAMPLE 26

Preparation of [6R,7R] 3-Methyl-7-phenoxyacetamidoceph-3-em-4-carboxylic Acid Diphenylmethyl Ester From [1S,3S,5R,6R] 2,2-Dimethyl-6-phenoxyacetamidopenam-3-carboxylic Acid-1-oxide Diphenylmethyl Ester Utilizing Various Isocyanates And Varying Amounts of Pyridine And Acetyl Bromide as Catalysts A solution of 55 gm (100 mmol) of [1S,3S,5R,6R] 2,2-dimethyl-6-phenoxyacetamidopenam-3-carboxylic acid-1-oxide diphenylmethyl ester in dioxane (500 ml) was dried over Linde 4A sieves (50 gm). Aliquots (25 ml each; 5 mmols) were withdrawn, charged with 15 mmoles (300 mole %) of the indicated isocyanate and the indicated mole percentage of pyridine and acetyl bromide. The solutions were refluxed under nitrogen for 6 hours and then concentrated in vacuo to dryness. The residues were filtered through silica gel (10 gm) with methylene chloride:acetone (9:1; v:v). The filtrates were concentrated in vacuo to light yellow foams which were analyzed by liquid chromatography against authentic [6R,7R] 3-methyl-7-phenoxyacetamidoceph-3-em-4-carboxylic acid diphenylmethyl ester as a standard. Listed below are the % weight yield, % activity and % activity yield for each reaction.

| Mole % Pyridine | Mole % $CH_3CBr=O$ | % Weight Yield | % Activity | % Activity Yield |
|---|---|---|---|---|
| Methanesulfonyl isocyanate | | | | |
| 10 | 5 | 110 | 47.2 | 52 |
| 30 | 25 | 110 | 47.8 | 53 |
| 50 | 25 | 130 | 37.5 | 49 |
| 100 | 50 | 120 | 27.6 | 33 |
| Trichloroacetyl isocyanate | | | | |
| 20 | 10 | 95 | 37.4 | 36 |
| 25 | 20 | 165 | 28.2 | 48 |
| 50 | 25 | 110 | 41.3 | 45 |
| Silicon tetraisocyanate | | | | |
| 20 | 10 | 120 | 43.2 | 52 |
| 30 | 25 | 120 | 51.0 | 61 |

I claim:
1. A compound of the formula

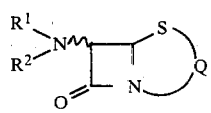

in which Q is

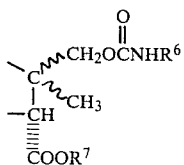

R[1] is hydrogen and R[2] is hydrogen, a conventional amino-protecting group, phenoxyacetyl, phenylacetyl, 2-amino-2-phenylacetyl, 2-amino-2-(p-hydroxyphenyl)acetyl, naphthoyl, 2-ethoxynaphthoyl, 5-methyl-3-phenyl-4-isoxazolylcarbonyl, 5-methyl-3-(o-chlorophenyl)-4-isoxazolylcarbonyl or 3-(2,6-dichlorophenyl)-5-methyl-4-isoxazolylcarbonyl, or R[1] and R[2], taken together with the nitrogen atom to which they are attached, form a phthalimido group, a succinimido group or a group of the formula

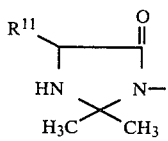

in which R[11] is phenyl or p-hydroxyphenyl;

R[6] is hydrogen, (lower)alkanoyl, chloroacetyl, dichloroacetyl, trichloroacetyl or p-toluenesulfonyl; and R[7] is hydrogen or a conventional carboxyl-protecting group;

or, when R[7] is hydrogen, a nontoxic pharmaceutically acceptable salt or physiologically hydrolyzable ester thereof.

2. A compound of claim 1 in which R[7] is hydrogen, and R[1] and R[2], taken together with the nitrogen to which they are attached, form a group of the formula

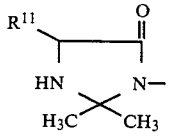

in which R[11] is phenyl or p-hydroxyphenyl; or a pharmaceutically acceptable salt or physiologically hydrolyzable ester thereof.

3. A compound of claim 2 in which R[6] is hydrogen; or a pharmaceutically acceptable salt or physiologically hydrolyzable ester thereof.

4. A compound of claim 1 having the formula

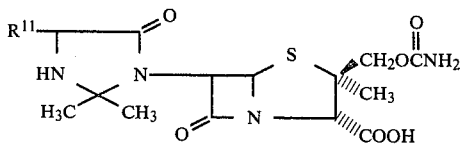

in which R[11] is phenyl or p-hydroxyphenyl; or a pharmaceutically acceptable salt or physiologically hydrolyzable ester thereof.

5. A compound of claim 1 having the formula

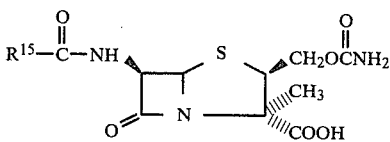

in which R[15] is benzyl, p-hydroxybenzyl, 5-methyl-3-phenyl-4-isoxazolyl, 5-methyl-3-(o-chlorophenyl)-4-isoxazolyl, 3-(2,6-dichlorophenyl)-5-methyl-4-isoxazolyl or 2-ethoxynaphthyl, or a nontoxic pharmaceutically acceptable salt or physiologically hydrolyzable ester thereof.

6. A compound of claim 1 having the formula

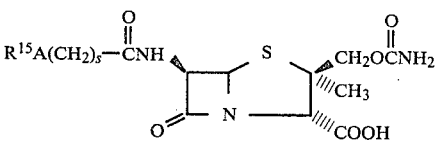

wherein R[15]A(CH$_2$)$_s$— is phenoxymethyl, or a nontoxic pharmaceutically acceptable salt or physiologically hydrolyzable ester thereof.

7. A compound of claim 1 having the formula

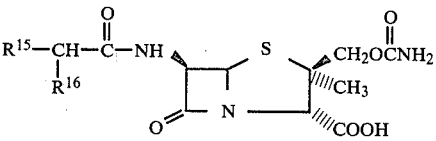

in which

is α-aminobenzyl or α-amino-p-hydroxybenzyl, or a nontoxic pharmaceutically acceptable salt or physiologically hydrolyzable ester thereof.

* * * * *

UNITED STATES PATENT AND TRADEMARK OFFICE
CERTIFICATE OF CORRECTION

PATENT NO. : 4,322,347
DATED : March 30, 1982
INVENTOR(S) : Robert L. Cundall et al.

It is certified that error appears in the above—identified patent and that said Letters Patent is hereby corrected as shown below:

In Column 4, at Line 30, the structure should be shown as

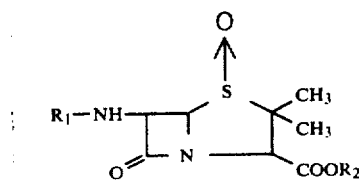

In Table 1, delete "31>", which is the third entry from the bottom in the column headed S. pneumoniae.

In Column 26, at Line 63, the moiety should be shown as (1, s, 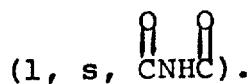).

In Column 27, at Line 3, the moiety should be shown as (2, s, 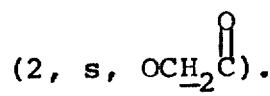).

In Column 27, at Line 36, the moiety should be shown as (2, s, 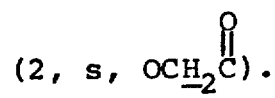).

In Column 28, at Line 38, the moiety should be shown as (br s, 1, 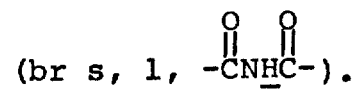).

UNITED STATES PATENT AND TRADEMARK OFFICE
CERTIFICATE OF CORRECTION

PATENT NO. : 4,322,347  
DATED : March 30, 1982  
INVENTOR(S) : Robert L. Cundall et al.

Page 2 of 3

It is certified that error appears in the above—identified patent and that said Letters Patent is hereby corrected as shown below:

In Column 30, at Line 30, the moiety should be shown as (2, s, 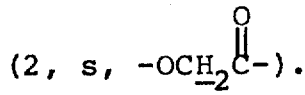).

In Column 31, at Line 23, the moiety should be shown as (s, 3 total, 1/2 aromatic AB pNB and 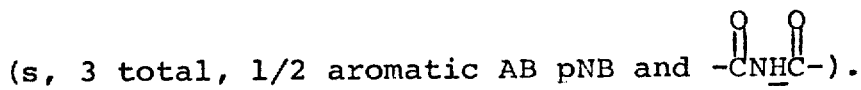).

In Column 31, at Line 66, the moiety should be shown as (2, s, 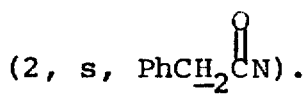).

In Column 32, at Line 24, the moiety should be shown as (1, br s, ).

In Column 32, at Line 36, the moiety should be shown as (3, s, 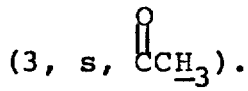).

In Column 36, at Line 44, the moiety should be shown as

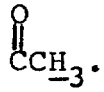.

UNITED STATES PATENT AND TRADEMARK OFFICE
CERTIFICATE OF CORRECTION

PATENT NO. : 4,322,347

DATED : March 30, 1982

INVENTOR(S) : Robert L. Cundall et al.

It is certified that error appears in the above—identified patent and that said Letters Patent is hereby corrected as shown below:

In Claim 5, the structure should be shown as

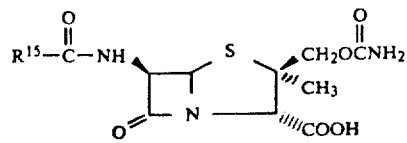

On the title page, Line [75] should read as follows:

Inventors: Robert L. Cundall, State College, Pennsylvania; Derek Walker, Jamesville, New York.

Signed and Sealed this

Twenty-ninth Day of June 1982

[SEAL]

Attest:

GERALD J. MOSSINGHOFF

Attesting Officer

Commissioner of Patents and Trademarks